(12) United States Patent
Wada

(10) Patent No.: US 10,012,662 B2
(45) Date of Patent: *Jul. 3, 2018

(54) INCUBATOR, SCHEDULE MANAGEMENT METHOD, AND PROGRAM

(71) Applicant: NIKON CORPORATION, Tokyo (JP)

(72) Inventor: Yoichi Wada, Kawasaki (JP)

(73) Assignee: NIKON CORPORATION, Tokyo (JP)

(*) Notice: Subject to any disclaimer, the term of this patent is extended or adjusted under 35 U.S.C. 154(b) by 73 days.

This patent is subject to a terminal disclaimer.

(21) Appl. No.: 14/966,447

(22) Filed: Dec. 11, 2015

(65) Prior Publication Data

US 2016/0131670 A1    May 12, 2016

Related U.S. Application Data

(63) Continuation of application No. 12/318,903, filed on Jan. 12, 2009, now Pat. No. 9,238,790, which is a
(Continued)

(30) Foreign Application Priority Data

Feb. 28, 2007 (JP) .................................. 2007-049023

(51) Int. Cl.
*G01N 35/00* (2006.01)
*C12M 1/34* (2006.01)
(Continued)

(52) U.S. Cl.
CPC ......... *G01N 35/0092* (2013.01); *C12M 23/50* (2013.01); *C12M 41/14* (2013.01);
(Continued)

(58) Field of Classification Search
CPC .... C12M 41/14; C12M 23/48; C12M 1/3446; C12Q 1/04; B01L 7/52; B01L 7/00;
(Continued)

(56) References Cited

U.S. PATENT DOCUMENTS 8,541,228 B2    9/2013 Kiyota
9,238,790 B2 *  1/2016 Wada .................... C12M 23/50
(Continued)

FOREIGN PATENT DOCUMENTS

JP    2006-011415 A    1/2006
JP    2006-029877 A    2/2006
(Continued)

OTHER PUBLICATIONS

Mar. 30, 2011 Office Action issued in U.S. Appl. No. 12/318,903.
(Continued)

*Primary Examiner* — Michael L Hobbs
(74) *Attorney, Agent, or Firm* — Oliff PLC

(57) ABSTRACT

An input section of an incubator accepts, from a user, a first input selecting a specified incubation container which registers an observing schedule, and a second input specifying an imaging condition of the specified incubation container in an observing sequence. A calculating section calculates, according to the above-mentioned imaging condition, an observing duration of the specified incubation container from a first data relating to a carrying period of an incubation container and a second data with regard to an imaging duration. A schedule management section extracts, based on a schedule data, a registrable time zone in which an observing sequence of the specified incubation container can be executed without overlapping with previously registered observing schedules, and outputs to display the registrable time zone for presentation to the user.

18 Claims, 13 Drawing Sheets

Related U.S. Application Data continuation of application No. PCT/JP2008/000349, filed on Feb. 26, 2008.

(51) Int. Cl.
  *C12M 1/00* (2006.01)
  *C12M 1/36* (2006.01)
  *G01N 35/02* (2006.01)

(52) U.S. Cl.
  CPC ............ *C12M 41/36* (2013.01); *C12M 41/48* (2013.01); *G01N 35/028* (2013.01); *G01N 2035/0094* (2013.01); *G01N 2035/0096* (2013.01); *G01N 2035/0097* (2013.01); *G01N 2035/00356* (2013.01)

(58) Field of Classification Search
  CPC ........ B01L 2300/0829; G01N 21/6428; G01N 21/6452; G01N 21/253
  See application file for complete search history.

(56) References Cited

U.S. PATENT DOCUMENTS

2005/0282268 A1    12/2005   Kagayama
2011/0205351 A1     8/2011   Nakamura et al.

FOREIGN PATENT DOCUMENTS

JP     2007-006852 A    1/2007
JP     2007-334141 A   12/2007

OTHER PUBLICATIONS

Oct. 5, 2011 Office Action issued in U.S. Appl. No. 12/318,903.
May 20, 2014 Office Action issued in U.S. Appl. No. 12/318,901.
Mar. 5, 2015 Office Action issued in U.S. Appl. No. 12/318,903.
Sep. 9, 2015 Notice of Allowance issued in U.S. Appl. No. 12/318,903.

\* cited by examiner

FIG. 19

INCUBATOR, SCHEDULE MANAGEMENT METHOD, AND PROGRAM

This is a continuation of U.S. application Ser. No. 12/318,903 filed on Jan. 12, 2009 (now U.S. Pat. No. 9,238,790), which is in turn a continuation of International Application No. PCT/JP2008/000349, filed Feb. 26, 2008, designating the U.S., and claims the benefit of priority from Japanese Patent Application No. 2007-049023, filed on Feb. 28, 2007, the entire contents of which are incorporated herein by reference.

BACKGROUND

1. Field

The present invention relates to an incubator comprising a temperature-controlled room which can maintain the environment condition suitable for incubating samples, and peripheral technology thereof.

2. Description of the Related Art

Incubators comprising a temperature-controlled room are generally used to incubate samples such as various microorganisms or cells. In such a temperature-controlled room, it is common to simultaneously incubate samples in a plurality of incubation containers.

On the other hand, it has been proposed to provide the incubator with a function of automatically observing the sample within the incubation container. For example, Patent Document 1 (Japanese Unexamined Patent Application Publication No. 2006-11415) discloses an arrangement of an incubation microscope which automatically executes time lapse observing of samples.

When automating the observation of samples in the incubator, it becomes very important to control the observing schedule. Particularly, overlap of observing schedules for a plurality of incubation containers may raise the possibility that samples can not be recorded with the time zone and number of times of observations desired by the user, whereby availability of the device substantially decreases. The above-mentioned Patent Document 1 has not sufficiently given consideration to prevent overlap of observing schedules, which leaves room for improvement at this point.

SUMMARY

The present invention is proposed to solve the above-mentioned problems in the prior-art. It is a proposition of the present invention to provide a means which can preliminarily prevent overlap of schedules for observing samples in the incubator.

A first Incubator of the invention includes a temperature-controlled room, an imaging section, a carrying mechanism, a controlling section, a first memory, a second memory, an input section, a calculating section, and a schedule management section. The temperature-controlled room has a storage section capable of housing a plurality of incubation containers, and can maintain its interior to a predefined environment condition. The imaging section captures images of the condition of samples within the incubation container in the temperature-controlled room. The carrying mechanism moves the incubation container between the storage section and the imaging section. The controlling section controls the imaging section and the carrying mechanism to automatically execute an observing sequence of the incubation container. The first memory records first data with regard to a carrying period of the incubation container by the carrying mechanism, and second data with regard to an imaging duration of the imaging section. The second memory records the schedule data. In the schedule data, an observing schedule indicating a start time and an observing duration of the observing sequence is registered in association with each of the incubation containers. The input section accepts, from the user, a first input selecting a specified incubation container for which the observing schedule is to be registered and a second input specifying an imaging condition of the specified incubation container in the observing sequence. The calculating section calculates the observing duration of the specified incubation container from the first data and the second data according to the imaging condition. The schedule management section extracts, based on the schedule data, a registrable time zone in which the observing sequence of the specified incubation container can be executed without overlapping with previously registered observing schedules. In addition, the schedule management outputs to display the registrable time zone for presentation to the user.

The second invention is arranged such that the schedule management section of the first invention registers, based on a user's input, the observing schedule of the specified incubation container into the schedule data, and disables registration of the observing schedule other than during the registrable time zone.

The third invention is arranged such that the calculating section of the second invention recalculates the observing duration of the specified incubation container if there is an input changing the imaging condition after registration of the observing schedule. In addition, the schedule management section outputs a notification to warn the user when overlap of observing schedules occurs due to increase of the observing duration.

The fourth invention is arranged such that the carrying mechanism of the first invention carries the incubation container out from the temperature-controlled room, according to the user's input. In addition, while the observing sequence of the incubation container to be carried out is being executed, the schedule management section outputs the notification to warn the user before carrying out the incubation container.

The fifth invention is arranged such that the schedule management section of the first invention displays a registration status of the observing schedule with regard to any of the incubation containers, based on the schedule data.

The sixth invention is arranged such that the incubator of the first invention further includes a communication section which can communicate with an external computer. The communication section then receives the first input and the second input from the computer, and transmits to the computer a display output indicating the registrable time zone.

The seventh invention is arranged such that the input section of the first invention further accepts a third input defining a condition of a time-lapse observing of the specified incubation container. In addition, the schedule management section sets a plurality of observing schedules of the specified incubation containers respectively having different observing times, according to the condition of the time-lapse observing. The schedule management section then extracts a registrable time zone in which each of the observing schedules of the time-lapse observing can be executed without overlapping with previously registered observing schedules.

The eighth invention is arranged such that the schedule management section of the seventh invention outputs to display, as the registrable time zone in the time-lapse observing, a first-time time zone of the time-lapse observing.

The ninth invention is arranged such that the schedule management section of the seventh invention outputs at least one of a warning and a presentation of the condition of the time-lapse observing for which the registrable time zone can be extracted, when the registrable time zone cannot be extracted.

The tenth invention is arranged such that the schedule management section of the seventh invention shifts one of the observing schedules of the time-lapse observing, when the registrable time zone cannot be extracted.

The incubator of the eleventh invention includes a temperature-controlled room, an imaging section, a carrying mechanism, a controlling section, a first memory, a second memory, an input section, a calculating section, and a schedule management section. The temperature-controlled room has a storage section capable of housing a plurality of incubation containers, and can maintain its interior to a predefined environment condition. The imaging section captures images of the condition of samples within the incubation container in the temperature-controlled room. The carrying mechanism moves the incubation container between the storage section and the imaging section. The controlling section controls the imaging section and the carrying mechanism to automatically execute an observing sequence of the incubation container. The first memory records first data with regard to carrying period of the incubation container by the carrying mechanism, and second data with regard to imaging duration of the imaging section. The second memory records the schedule data. In the schedule data, an observing schedule indicating a start time and an observing duration of the observing sequence is registered in association with each of the incubation containers. The input section accepts, from the user, a first input selecting a specified incubation container for which the observing schedule is to be registered, a second input specifying the imaging condition of the specified incubation container in the observing sequence, and a third input defining a condition of a time-lapse observing of the specified incubation container and the start time of the time-lapse observing. The calculating section calculates the observing duration of the specified incubation container from the first data and the second data, according to the imaging condition. The schedule management section tentatively sets a schedule of the time-lapse observing of the specified incubation container, according to the third input and the observing duration. In addition, the schedule management section determines, based on the schedule data, whether or not the tentatively set schedule of the time-lapse observing overlaps with previously registered observing schedules.

The twelfth invention is arranged such that the schedule management section of the eleventh invention outputs a warning if the schedule of the time-lapse observing overlaps with previously registered observing schedules.

The thirteenth invention is arranged such that the schedule management section of the twelfth invention resets the schedule of the time-lapse observing by modifying at least one of either the condition of the time-lapse observing or the start time of the time-lapse observing, when the schedule of the time-lapse observing overlaps with previously registered observing schedules.

The fourteenth invention is arranged such that the schedule management section of the twelfth invention outputs to display overlapping portions of the schedule, when the schedule of the time-lapse observing overlaps with previously registered observing schedules.

The fifteenth invention is arranged such that the schedule management section of the eleventh invention records the schedule of the time-lapse observing into the second memory, when the schedule of the time-lapse observing does not overlap with previously registered observing schedules.

Note that, those expressing the concept of respective inventions as interpretation into a schedule management method or a computer program relating to observation of incubation containers, are also effective as concrete aspects of the present invention.

According to an aspect of the present invention, a registrable time zone which does not overlap with previously registered observing schedules is presented to the user, based on the observing duration according to the imaging condition, whereby overlap of schedules can be preliminarily prevented.

In addition, according to another aspect of the present invention, registration of a schedule of the time-lapse observing which causes overlapping with previously registered observing schedules can be preliminarily prevented.

BRIEF DESCRIPTION OF THE DRAWINGS

FIG. 19 illustrates an exemplary display screen relating to time-lapse observing.

DETAILED DESCRIPTION OF THE EMBODIMENTS

Description of First Embodiment (Arrangement of Incubator of First Embodiment)

Figure 1:
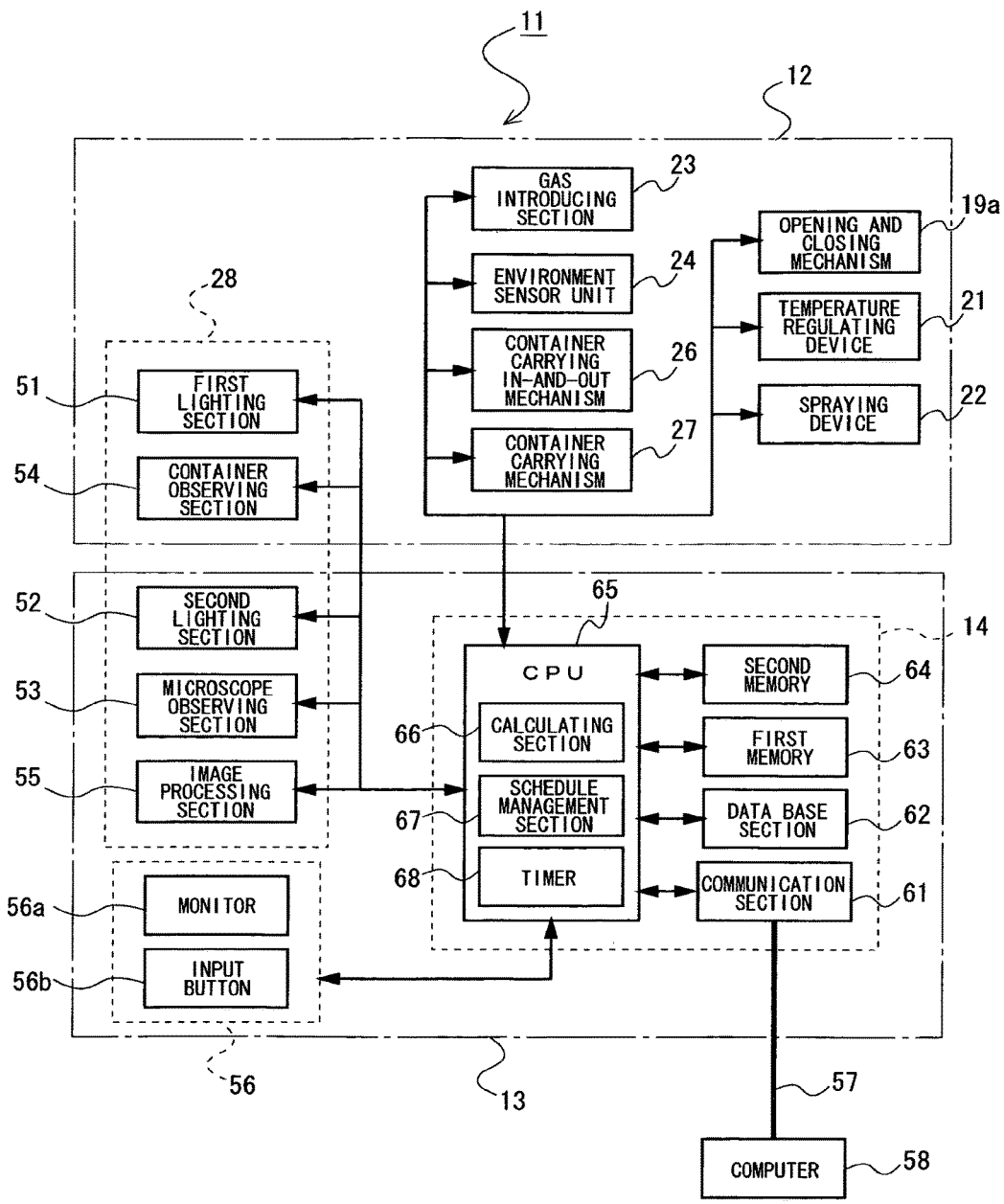
FIG. 1 is a block diagram of the incubator of a first embodiment.
Figure 2:
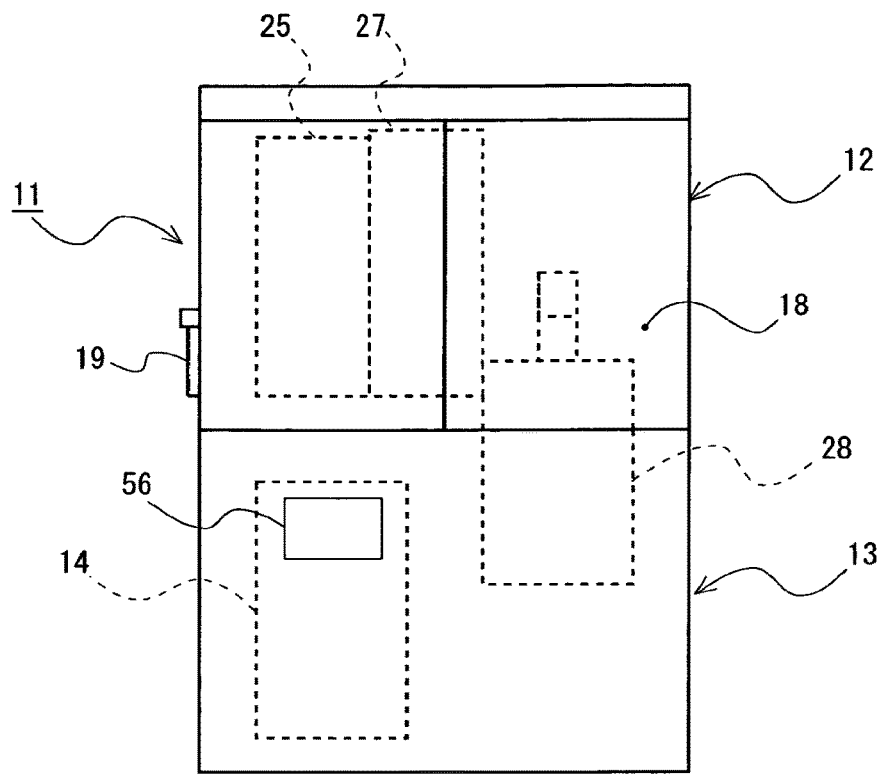
FIG. 2 is a front view of the incubator of the first embodiment.
Figure 3:
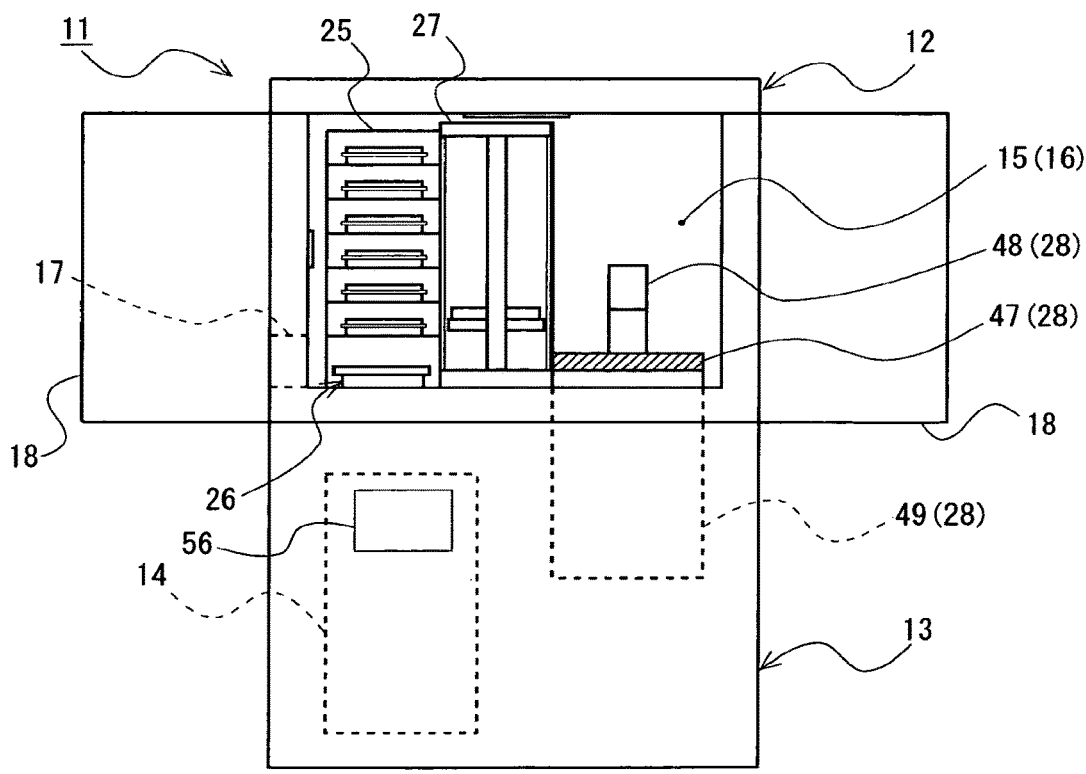
FIG. 3 illustrates the front door of FIG. 2 in the open state.

An arrangement of the incubator of a first embodiment will be described below in detail, referring to the drawings. FIG. 1 is a block diagram of the incubator of the first embodiment. Additionally, FIGS. 2 and 3 are front views of the incubator of the first embodiment.

The incubator 11 of the first embodiment has a first enclosure 12 which incubates samples and a second enclosure 13 which houses a controlling unit 14. In the assembled state of the incubator 11, the first enclosure 12 is disposed on the second enclosure 13.

First, the general arrangement of the first enclosure 12 will be described.

A temperature-controlled room 15 covered with heat insulating material is formed inside the first enclosure 12. The temperature-controlled room 15 is in communication with the outside by a front opening 16 formed on the front face of the first enclosure 12 and a carrying in-and-out opening 17 formed on the left side face of the first enclosure 12 shown in FIGS. 2 and 3. The front opening 16 of the first enclosure 12 is covered by a clamshell front door 18 so that it can be opened or closed. In addition, the carrying in-and-out opening 17 of the first enclosure 12 is covered by a sliding automatic door 19 so that it can be opened or closed. Here, the size of the carrying in-and-out opening 17 is defined such that an incubation container (30) can pass through. An opening 20 is formed at the right-hand side of the base of the first enclosure 12 seen from the front face. In addition, an observing section (28) described below is disposed inside the temperature-controlled room 15 via the above-mentioned opening 20.

Figure 4:
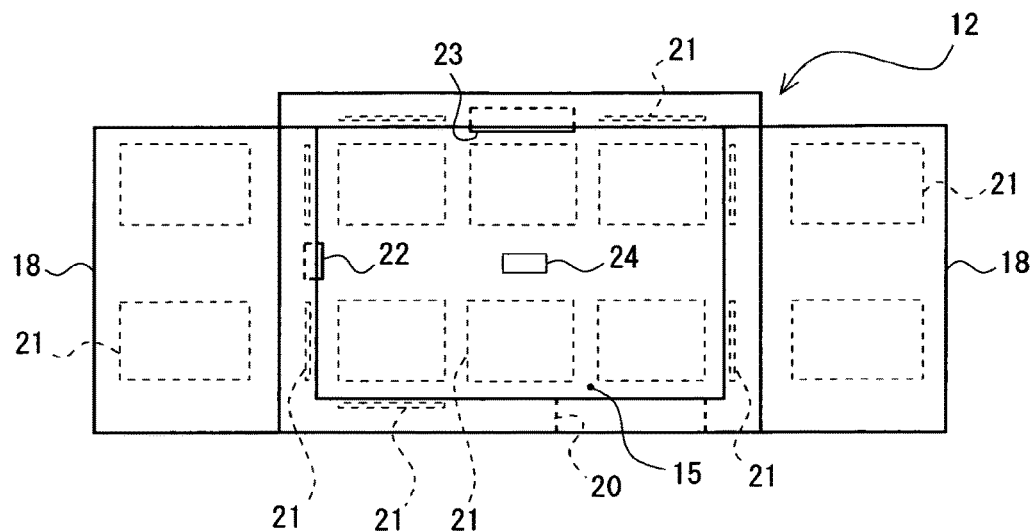
FIG. 4 illustrates the interior of the temperature-controlled room of the first enclosure.

FIG. 4 illustrates the interior of the temperature-controlled room 15 of the first enclosure 12. On the wall surface of the temperature-controlled room 15, a temperature regulating device 21, a spraying device 22, a gas introducing section 23, and an environment sensor unit 24 are built-in, respectively.

The temperature regulating device 21, having a Peltier element, heats and cools the temperature-controlled room 15 using Peltier effect. The spraying device 22 sprays inside the temperature-controlled room 15 to regulate the humidity inside the temperature-controlled room 15. The gas introducing section 23 is coupled to a carbon dioxide tank (not shown). The gas introducing section 23 regulates carbon dioxide concentration inside the temperature-controlled room 15 by introducing carbon dioxide into the temperature-controlled room 15. The environment sensor unit 24 detects temperature, humidity, and carbon dioxide concentration, respectively, inside the temperature-controlled room 15.

Returning to FIGS. 2 and 3, in the assembled state of the incubator 11, a stocker 25, a container carrying in-and-out mechanism 26, a container carrying mechanism 27, and a part of the observing unit 28 are respectively disposed inside the temperature-controlled room 15.

Figure 5:
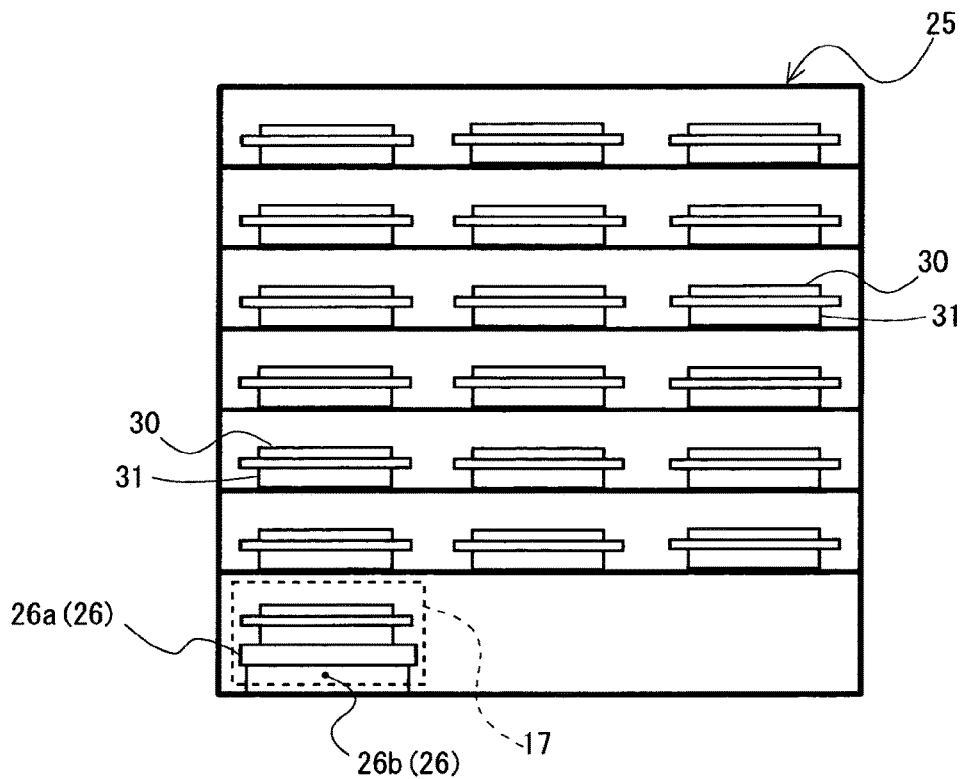
FIG. 5 illustrates the stocker seen from the side direction of the enclosure.
Figure 6A:
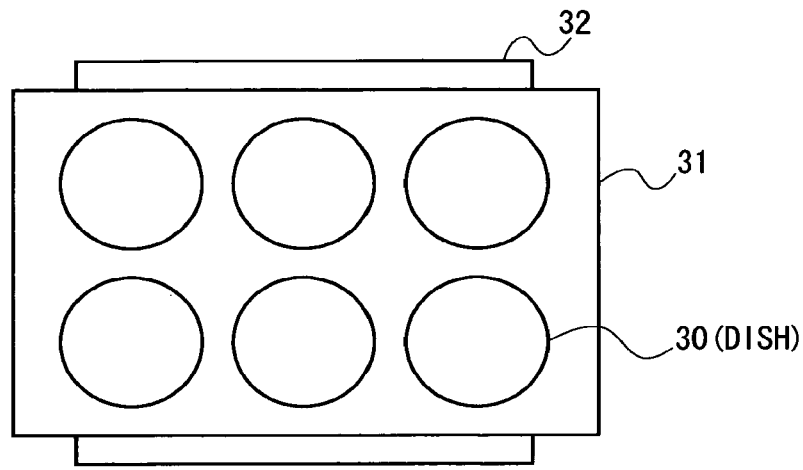
FIGS. 6 (*a*) to 6 (*c*) each illustrates an exemplary incubation container which incubates samples.
Figure 6B:
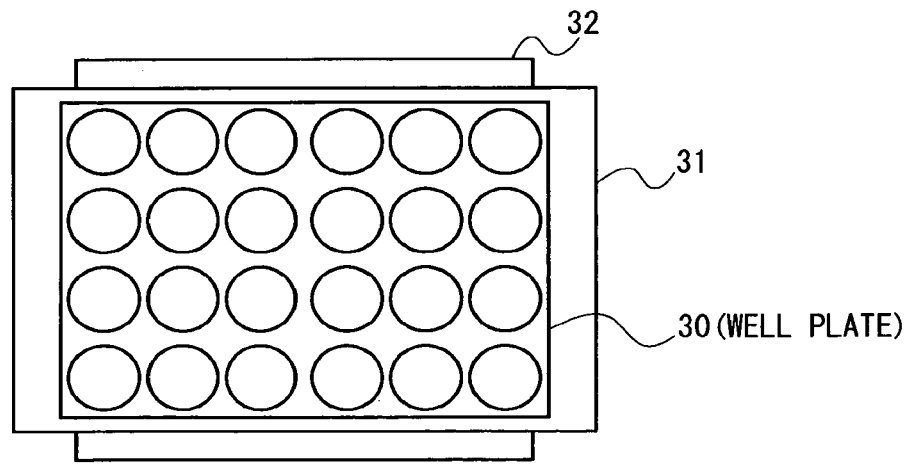
Figure 6C:
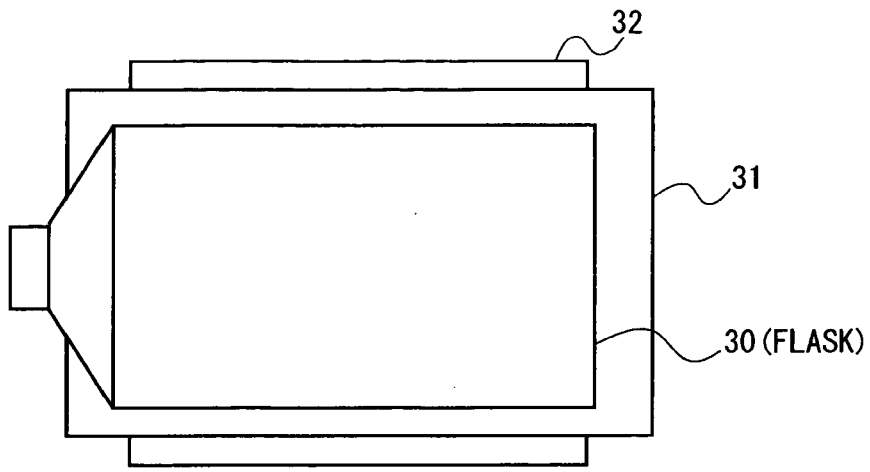

The stocker 25 is disposed on the left hand side of the temperature-controlled room 15 seen from the front face of the first enclosure 12. FIG. 5 illustrates the stocker 25 seen from the side face direction of the enclosure. The stocker 25 has a plurality of shelves, each of which capable of housing the incubation container 30. Here, FIGS. 6 (*a*) to 6 (*c*) each illustrates an exemplary arrangement of the incubation container 30 which incubates samples. A well plate, a flask, a dish or the like are used as the incubation container 30 of the first embodiment. Each incubation container 30 contains a sample (such as cell) to be incubated as well as the liquid culture medium. In addition, the above-mentioned incubation container 30 is placed and handled on a transparent tray-like holder 31. A supporting piece 32 facing outward is formed on each of both sides of the holder 31. Note that the incubation container 30 may have, depending on its type, a plurality of small containers, in which case each of the small containers can incubate a sample on a single holder 31.

Additionally, in the assembled state of the incubator 11, the lowest level of the stocker 25 corresponds to the position of the first carrying in-and-out opening 17 of the enclosure 12. A container carrying in-and-out mechanism 26 which carries the incubation container 30 is disposed in the space of the lowest level of the stocker 25. The container carrying in-and-out mechanism 26 has a carrying table 26a capable of placing the incubation container 30 and a holder 31, and a motor unit 26b which causes the carrying table 26a to move outside of the carrying in-and-out opening 17, reciprocatingly.

Figure 7A:
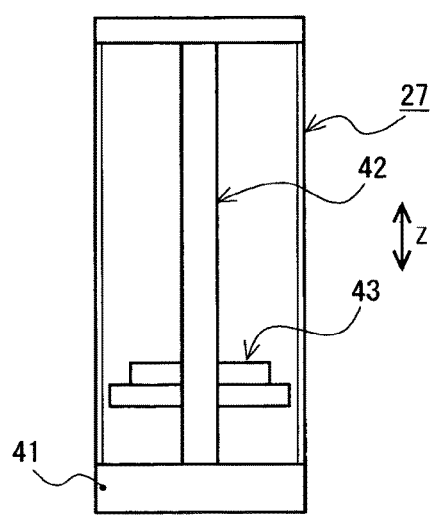
FIG. 7 (*a*) illustrates the container carrying mechanism from the frontal direction of the enclosure, and FIG. 7 (*b*) illustrates the container carrying mechanism from the planer direction of the enclosure.
Figure 7B:
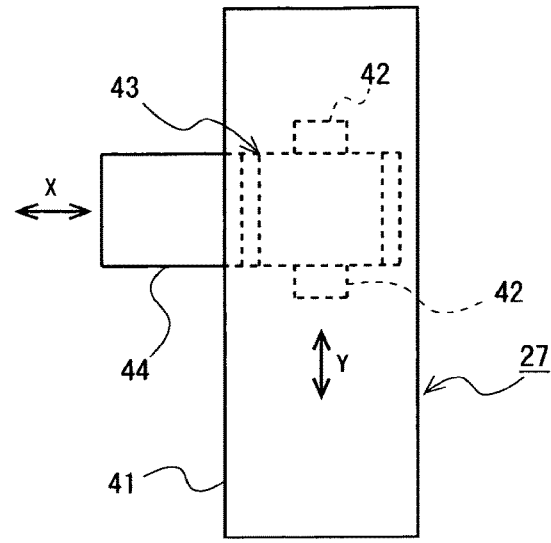
Figure 8:
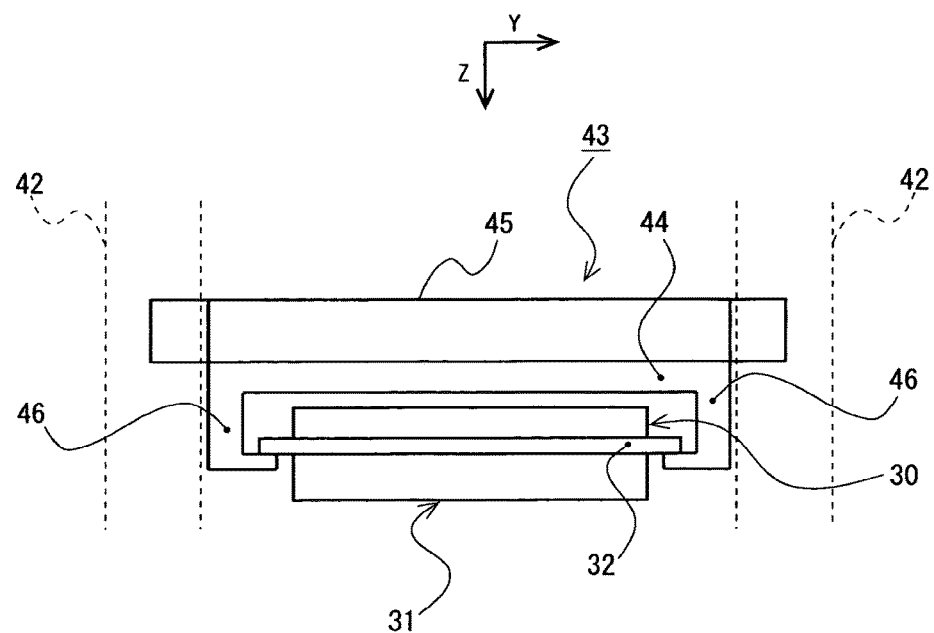
FIG. 8 is a front view illustrating the arrangement of the carrier arm section.
Figure 9:
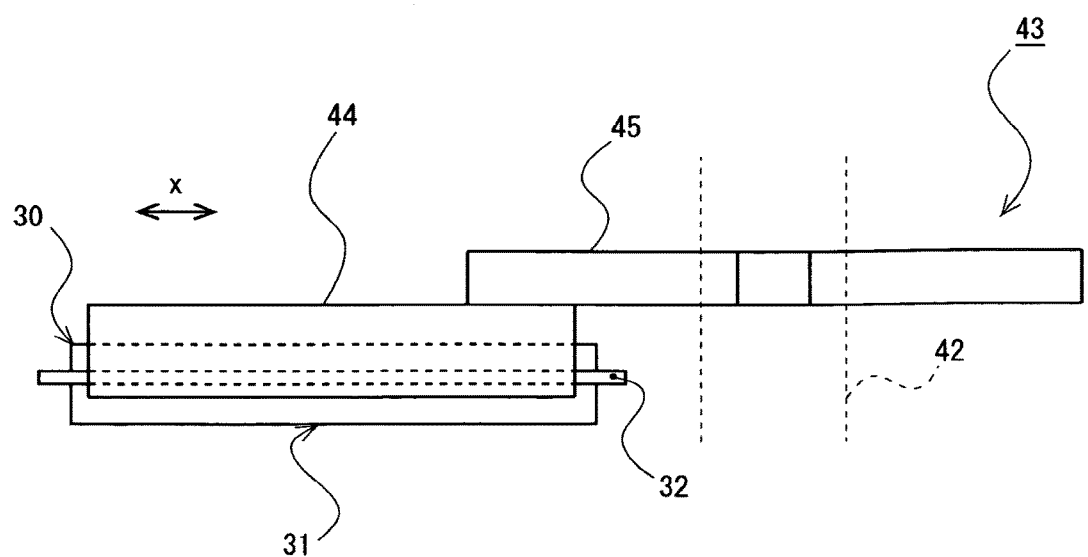
FIG. 9 is a side view illustrating the arrangement of the carrier arm section.

A container carrying mechanism 27 is disposed at the center of the temperature-controlled room 15 seen from the front face of the first enclosure 12. FIGS. 7 to 9 illustrate an arrangement of the container carrying mechanism 27. The container carrying mechanism 27 has a rectangular base platform 41, a vertical frame 42, and a carrier arm section 43. Here, each part of the container carrying mechanism 27 is driven by a motor (not shown) which is built in the base platform 41 or the like. In addition, position of each part of the container carrying mechanism 27 is monitored by a controlling unit 14 using an encoder 25 or the like.

A vertical frame 42 is mounted on the base platform 41 movably forward and backward (Y-direction in the figure). The vertical frame 42 includes a pair of guide rails extending upward and downward. A carrying arm section 43 is provided movably upward and downward (Z-direction in the figure) between the vertical frame 42.

In addition, the carrying arm section 43 has a container supporting section 44 and a sliding mechanism 45. The main body of the container supporting section 44 is made slightly wider than the entire width of the holder 31. A pair of hook nails 46 are formed downward at both side edges of the container supporting section 44. Thus, the container supporting section 44 is arranged so that it can support the holder 31 by engagement between the supporting piece 32 of the holder 31 and the hook nail 46. On the other hand, the sliding mechanism 45, disposed on the top face of the container supporting section 44, causes the container supporting section 44 to slide horizontally (X-direction in the figure). Due to such movement of the sliding mechanism 45, it becomes possible to pass the holder 31 having the incubation container 30 placed thereon between the container carrying mechanism 27 and any one of the stocker 25, the container carrying in-and-out mechanism 26, or the observing unit 28.

The observing unit 28 is disposed at the right-hand side of the temperature-controlled room 15 seen from the front face of the first enclosure 12. The observing unit 28 is fitted into the opening 20 at the bottom of the first enclosure 12. The observing unit 28 has a sample stage 47, an arm 48 protruding above the sample stage 47, and a main body 49. Then, the sample stage 47 and the arm 48 are disposed inside the temperature-controlled room 15 of the first enclosure 12, whereas the main body 49 is housed in the second enclosure 13.

Figure 10:
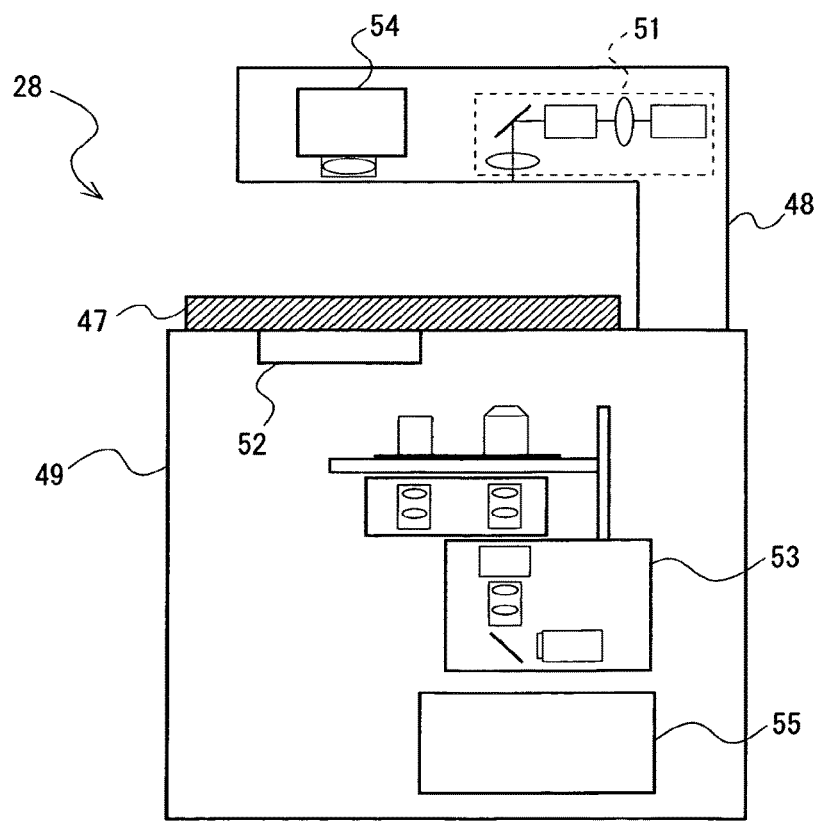
FIG. 10 is a schematic view illustrating the arrangement of the observing unit.

FIG. 10 is a schematic view illustrating an arrangement of the observing unit 28. The observing unit 28 has a sample stage 47, a first lighting section 51 and a second lighting section 52, a microscope observing section 53, a container observing section 54, and an image processing section 55.

The sample stage 47 is made of translucent material, with an incubation container 30 placed thereon together with the holder 31. The sample stage 47 is arranged movably horizontally (X-direction and Y-direction) so that it can adjust the position of the holder 31 relative to the microscope observing section 53 and the container observing section 54.

In addition, the first lighting section 51, which is disposed inside the arm 48, illuminates the incubation container 30 from above the sample stage 47. On the other hand, the second lighting section 52, which is built-in the main body 49, illuminates the incubation container 30 from below the sample stage 47.

The microscope observing section 53, which is built in the main body 49, has a microscope optical system and an image pickup device (all of which are not illustrated). The microscope observing section 53 captures images of samples observed through the microscope (microscope observing image) with the help of illumination light of the first lighting section 51.

The container observing section 54, which is housed in the arm 48, has an optical imaging system and an image pickup device (all of which are not illustrated). The container observing section 54 captures the entire observing image of the incubation container 30 with the help of illumination light of the second lighting section 52.

The image processing section 55 executes A/D conversion of images output from the microscope observing section 53 and the container observing section 54, and generates data of microscope observing images or entire observing images, respectively.

Next, the arrangement of the second enclosure 13 will be described in general. In the second enclosure 13, the main body 49 of the observing unit 28 and the controlling unit 14 are housed. In addition, an operation panel 56 comprising a monitor 56a and an input button 56b is disposed on the front face of the second enclosure 13. A computer 58 can be coupled to the controlling unit 14 via a communication line 57.

Here, the controlling unit 14 is coupled to a door opening and closing mechanism 19a of the automatic door 19, a temperature regulating device 21, a spraying device 22, a gas introducing section 23, an environment sensor unit 24, a container carrying in-and-out mechanism 26, a container carrying mechanism 27, an observing unit 28, a monitor 56a and an input button 56b of the operation panel 56, respectively. The controlling unit 14 executes overall control of each part of the incubator 11 according to a predefined program.

As an example, the controlling unit 14 controls the temperature regulating device 21, the spraying device 22, the gas introducing section 23, and the environment sensor unit 24 respectively, to maintain the temperature-controlled room 15 at a predefined environment condition. In addition, the controlling unit 14 controls the observing unit 28 and the container carrying mechanism 27 based on the observing schedule set by the user to automatically execute the observing sequence of the incubation container 30.

Here, the controlling unit 14 has a communication section 61, a data base section 62, a first memory 63 and a second memory 64, and a CPU 65. The communication section 61, the data base section 62, the first memory 63 and the second memory 64 are coupled to the CPU 65, respectively.

The communication section 61 executes transmission and reception of data between the computer 58 outside the incubator 11 via a wireless or wired communication line 57.

The data base section 62 records management data with regard to each of the incubation containers 30 housed in the stocker 25. The management data includes, for example, identification information of the incubation container 30 and the holder 31, type and shape of the incubation container 30, housing position of the incubation container 30 in the stocker 25, or the like.

In addition, a recording area for recording data files of microscope observing images and entire observing image and history information of environment condition (temperature, humidity, carbon dioxide concentration) inside the temperature-controlled room 15 is provided in the data base region 62. Here, in the above-mentioned data file, metadata indicating the identification information of the image-captured incubation container 30, time and date of image capturing, condition of image capturing or the like is associated with the image data.

The first memory 63 has a variety of data recorded therein to calculate the observing duration in the observing sequence. For example, the first memory 63 has first data with regard to carrying period of the incubation container 30 and second data with regard to duration of the imaging operation by the observing unit 28 recorded therein, respectively.

More specifically, carrying period of the first data is calculated by adding the time required for the container carrying mechanism 27 to carry the incubation container 30 from the stocker 25 to the observing unit 28 and the time corresponding to error margin. Although the carrying period of the incubation container 30 varies according to the housing position in the stocker 25, the above-mentioned carrying period is determined based on the case where the incubation container 30 is placed at the farthest position from the observing unit 28 (maximum value of respective carrying periods) in the first embodiment.

In addition, the second data has a table recorded therein, indicating the correspondence between the operation parameter with regard to the observing unit 28 and the duration corresponding to the parameter.

As an example, the second data of the first embodiment includes items such as (1) imaging period of the entire observing image by the container observing section 54, (2) positioning period of guiding the incubation container 30 to a predefined imaging position, (3) AF operation period of the microscope observing section 53 and the container observing section 54, (4) required time for changing the magnification of the objective lens of the microscope observing section 53, (5) imaging period when capturing images of a plurality of frames by changing the position of the microscope observing section 53 and the sample along the height direction, or the like. For each of the items (1) to (5) of the second data, values of duration are set, respectively, according to parameters such as imaging condition, device arrangement, and shape of the incubation container 30 or the like.

The second memory 64 has the schedule data of the above-mentioned observing sequence recorded therein. The schedule data has observing schedules indicating the start time and observing duration of each observing sequence recorded therein in association with the identification information of each holder 31. Here, each observing schedule is associated with data setting the imaging condition of the observing unit 28 in the observing sequence.

The CPU 65 is a processor which executes a variety of calculations of the controlling unit 14. The CPU 65 serves as the calculating section 66 which calculates the observing duration of the incubation container 30 and the schedule management section 67 which registers the observing schedule, in the registration processing of the observing schedule described below. Furthermore, the CPU 65 serves as a timer 68 for managing the observing schedule.

(Description of Registration Processing of Observing Schedule)

Figure 11:
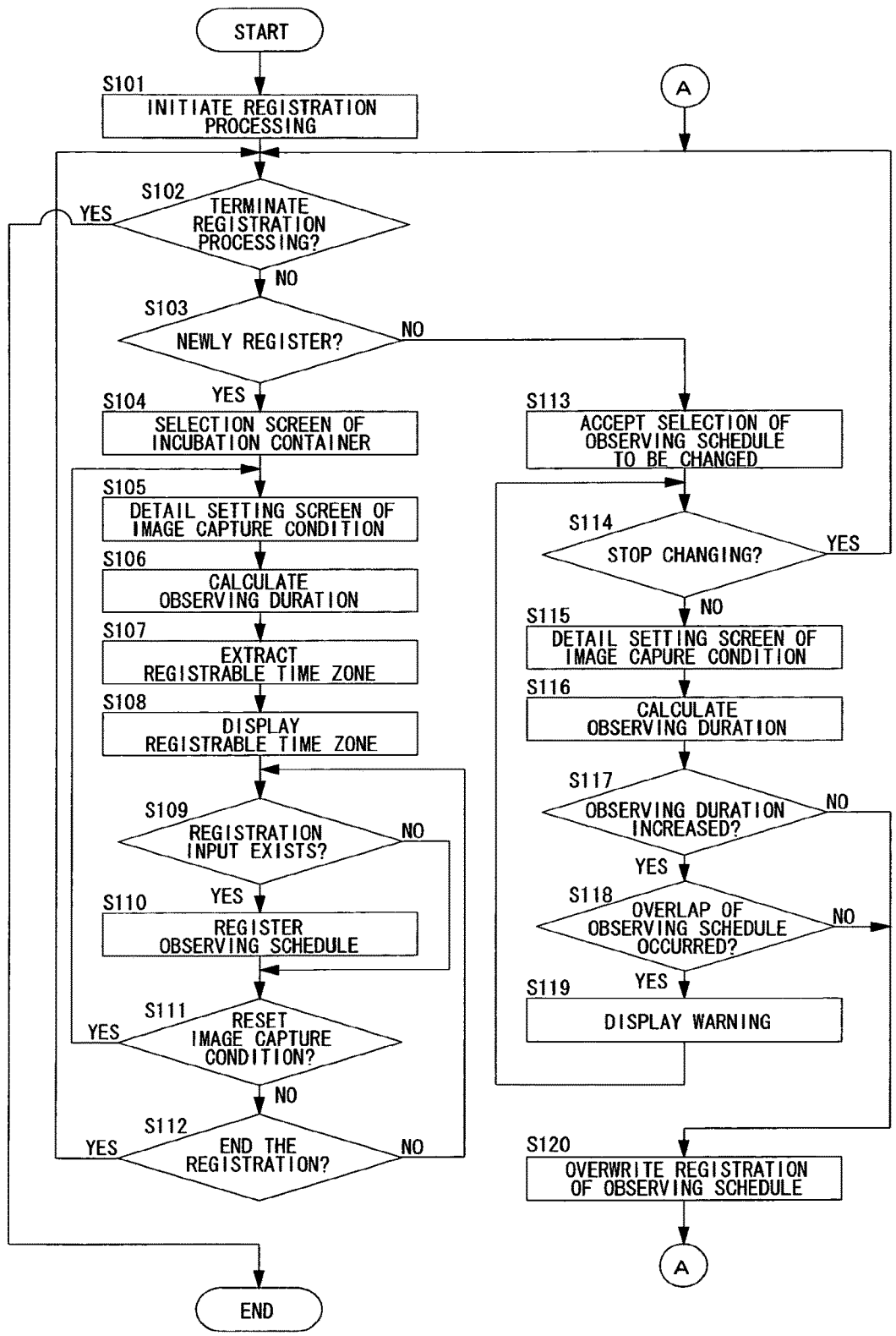
FIG. 11 is a flow chart explaining the operation of the CPU in the registration processing of the observing schedule.

In the following, operation of the CPU 65 in the registration processing of the observing schedule will be described, referring to the flow chart of FIG. 11. Here, the registration manipulation of the observing schedule of the incubation container 30 is performed by the user from the operation panel 56 of the incubator 11 or from the computer 58 coupled to the incubator 11.

Step 101: The CPU 65 of the controlling unit 14 initiates the registration processing of the observing schedule in response to the user's manipulation. In this occasion, the CPU 65 displays a prompt to select among "newly register observing schedule", "change previously registered observing schedule", and "terminate registration processing", on the monitor 56a of the operation panel 56 (or a monitor of the computer 58). The CPU 65 then proceeds to S102 upon accepting any of the selection inputs of the above-mentioned items from the input button 56b of the operation panel 56 (or an input device of the computer 58).

Step 102: The CPU 65 determines whether or not an input to "terminate registration processing" is accepted. If the above condition is satisfied (the case of YES), the CPU 65 terminates the registration processing of the observing schedule. If, on the other hand, an input selecting another item is accepted (the case of NO), the CPU 65 proceeds to S103.

Step 103: The CPU 65 determines whether or not an input to "newly register observing schedule" is accepted. If the above condition is satisfied (the case of YES), the CPU 65 proceeds to S104. If, on the other hand, the input to "change previously registered observing schedule" is accepted (the case of NO), the CPU 65 proceeds to S113.

Step 104: The CPU 65 displays a selection screen letting the user select an incubation container 30 for which an observing schedule is to be set, on the monitor 56a of the operation panel 56 (or a monitor of the computer 58).

Figure 12:
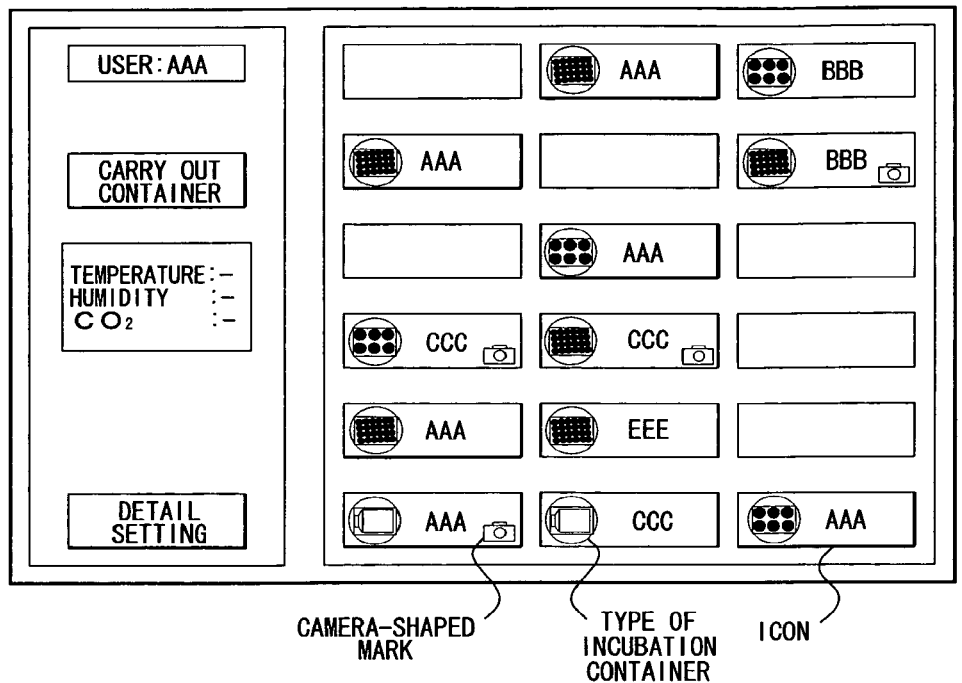
FIG. 12 illustrates an exemplary selection screen in S104.

Here, an exemplary selection screen in S104 is shown in FIG. 12. On the selection screen, an incubation container 30 for which an observing schedule is to be set is displayed as an icon of GUI (Graphical User Interface) form. The location of the icon on selection screen corresponds to the location of the incubation container 30 in the stocker 25. Then, the user can specify, to the CPU 65, the incubation container 30 for which an observing schedule is to be set, by selecting the above-mentioned icon. Here, the CPU 65 proceeds to S105 upon accepting an input selecting the incubation container 30 in S104.

In the selection screen of FIG. 12, a classification mark indicating the type of the incubation container 30 is displayed on each icon. Furthermore, a camera-shaped mark is displayed on the icon of an incubation container 30 having an observing schedule registered in the schedule data. In addition, when the incubator 11 is used by a plurality of users, each of the incubation containers 30 may have user IDs registered therewith. In this case, only the incubation container 30 corresponding to the user ID will have an observing schedule set thereto on the selection screen of FIG. 12. Here, the user's input in the selection screen is provided from the input button 56b of the operation panel 56 (or an input device of the computer 58).

Step 105: The CPU 65 displays the detail setting screen of imaging condition on the monitor 56a of the operation panel 56 (or a monitor of the computer 58).

Figure 13:
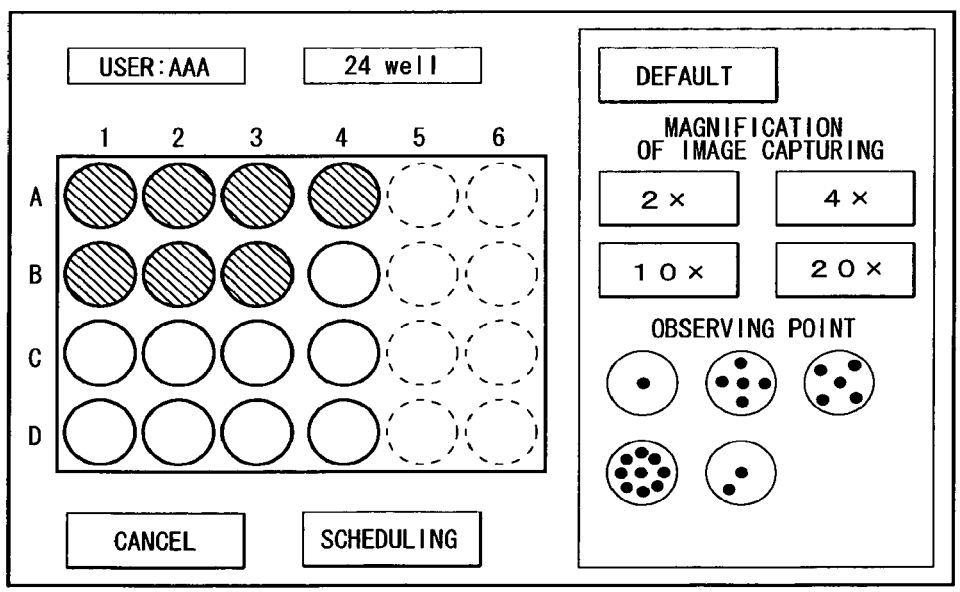
FIG. 13 illustrates an exemplary detail setting screen of imaging condition in S105.

Here, an exemplary detail setting screen of imaging condition in S105 is shown in FIG. 13. In the detail setting screen of imaging condition, an icon indicating the shape of the incubation container 30 is displayed on the left half of the screen. In addition, an icon for specifying the imaging condition is displayed on the right half of the detail setting screen.

With the icon indicating the shape of the incubation container 30, the user can instruct the CPU 65 which of the containers should be image-captured when there are a plurality of containers on the holder 31.

On the other hand, with the icon on the right half of the detailed setting screen, the user can specify, to the CPU 65, (1) the magnification (2-, 4-, 10-, 20-times) of the objective lens of the microscope observing section 53, and (2) the observing point in the container. Additionally, the user's selecting a default item of FIG. 13 is followed by an input into the CPU 65 of an initially set imaging condition (for example, five-point observing by a 10- or 20-times objective lens). Here, the observing point may be customized by the user.

In addition, when the detail setting screen of imaging condition is displayed, the user can simultaneously define the number of frames of the microscope observing image to be image-captured by the microscope observing section 53. Here, the user's input in the detail setting screen of imaging condition is provided from the input button 56b of the operation panel 56 (or an input device of the computer 58).

Step 106: The CPU 65 calculates the observing duration of the incubation container 30.

Specifically, the CPU 65 acquires, from the first data of the first memory 63, the carrying period for a round trip of the incubation container 30 in the observing sequence. Additionally, based on the imaging condition set in S105, the CPU 65 acquires the duration corresponding to the parameter of imaging condition from the second data of the first memory 63. The CPU 65 then adds the duration acquired from the first data and the second data. Subsequently, the CPU 65 rounds up the fraction of the above-mentioned duration so that it becomes a multiple number of the unit time (10 minutes, for example) of the schedule data to acquire the final observing duration.

Step 107: The CPU 65 extracts a registrable time zone. Specifically, the CPU 65 first extracts, from the schedule data of the second memory 64, all the idle-time having no observing schedule registered therein. Then the CPU 65 extracts, from the above-mentioned idle-time, time zones equal to or longer than the observing duration (the one acquired in S106) as registrable time zones.

Here, when observing schedules of incubation containers 30 having a common holder 31 are registered in succession, the processing of carrying the incubation container 30 into and out from the stocker 25 between two observing schedules becomes needless.

Therefore, in the above case, the CPU 65 calculates the registrable time zone after preliminarily subtracting the carrying period in one of the observing schedules.

Step 108: The CPU 65 displays, on the monitor 56a of the operation panel 56 (or a monitor of the computer 58) the registrable time zone acquired in S107.

Figure 14:
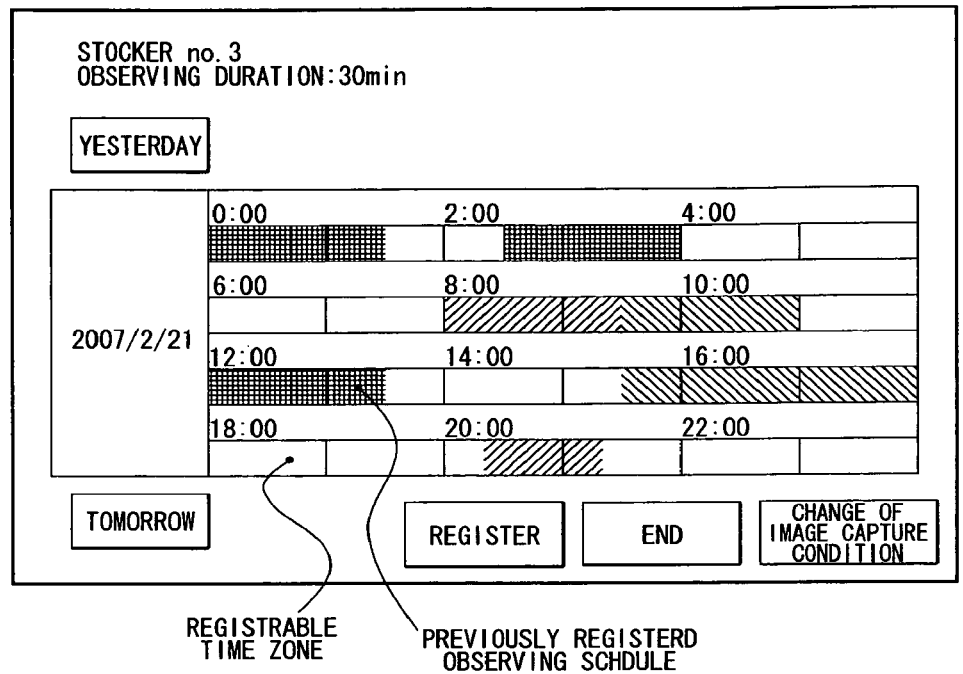
FIG. 14 illustrates an exemplary display screen of the registrable time zone in S108.

Here, an exemplary display screen of the registrable time zone in S108 is shown in FIG. 14. On the display screen of the registrable time zone, the previously registered observing schedule and the above-mentioned registrable time zone are displayed as a list. In FIG. 14, the previously registered observing schedule is shown by hatching, whereas the registrable time zone is shown as blank fields.

Then, the user can register an observing schedule in the second memory 64 by specifying a desired time zone among the registrable time zones. Here, the user's input on the display screen of the registrable time zones is performed via the input button 56b of the operation panel 56 (or an input device of the computer 58).

Here, on the display screen of registrable time zones, the CPU 65 preliminarily disables registration of an observing schedule other than during the registrable time zone.

In other words, registration of a new observing schedule in a time zone overlapping with previously registered observing schedules is prohibited in the display screen of registrable time zones.

Step 109: The CPU 65 determines whether or not an input to register an observing schedule (for example, input via the registration button in FIG. 14) is accepted with the display screen of S108 being displayed. If an observing schedule is registered (the case of YES), the CPU 65 proceeds to S110. If, on the other hand, no observing schedule is registered (the case of NO), CPU 65 proceeds to S111.

Figure 15:
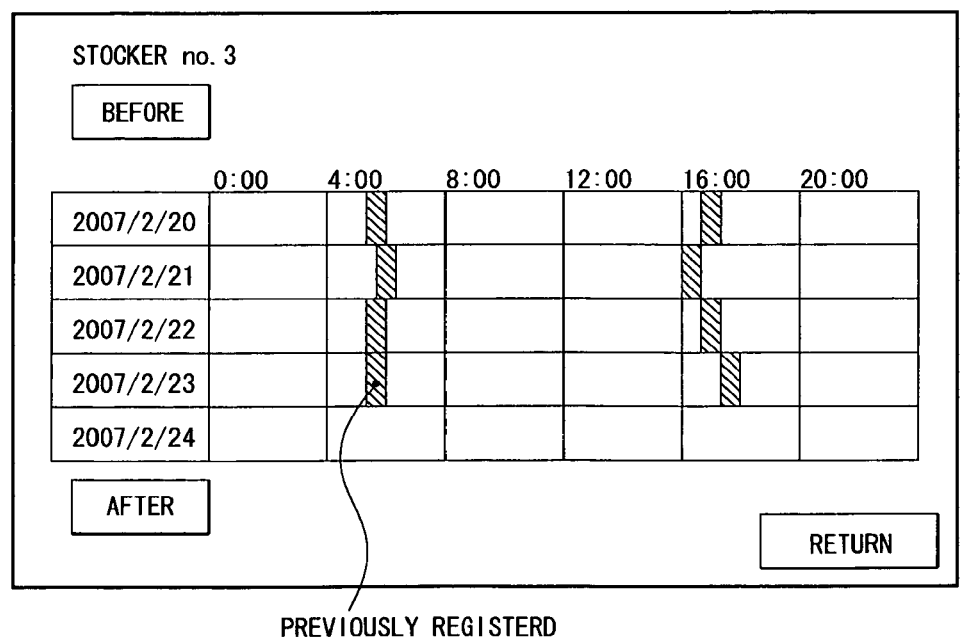
FIG. 15 illustrates a display screen of the registration status of observing schedule relating to predefined incubation container.

Step 110: The CPU 65 registers the observing schedule in the schedule data of the second memory 64. Here, according to the user's manipulation, the CPU 65 can also display a list of registration status of observing schedules relating to any of the incubation containers 30 (see. FIG. 15) on the monitor 56a of the operation panel 56 (or a monitor of the computer 58). Displaying the list of observing schedules allows the user to grasp the observing schedule of the incubation container 30 more easily, whereby enhancing user-friendliness of the device.

Step 111: The CPU 65 determines whether or not an input to reset the imaging condition (for example, input via the change imaging condition button in FIG. 14) is accepted with the display screen of S108 being displayed. If there is an input to reset the imaging condition (the case of YES), the CPU 65 returns to S105 and repeats the above-mentioned operation. If, on the other hand, there is no input to reset the imaging condition (the case of NO), the CPU 65 proceeds to S112.

Step 112: The CPU 65 determines whether or not an input to terminate the registration (for example, input from END button in FIG. 14) is accepted with the display screen of S108 being displayed. If there is an input to terminate the registration (the case of YES), the CPU 65 returns to S102 and repeats the above-mentioned operation.

If, on the other hand, there is no input ending the registration (the case of NO), the CPU 65 returns to S109 and repeats the above-mentioned operation. That is, in this case (the case of NO in S112), the user is allowed to sequentially register, on the display screen of S108, observing schedules with regard to the same incubation container 30 in the CPU 65.

Step 113: The CPU 65 displays a screen for accepting selection of the observing schedule to be changed on the monitor 56a of the operation panel 56 (or a monitor of the computer 58). For example, the CPU 65 displays in S113 a display screen listing the observing schedules (the screen substantially similar to FIG. 14), letting the user directly specify an observing schedule to be changed.

The CPU 65 in S113 may let the user select an incubation container 30 in the selection screen of FIG. 12 to narrow down the previously registered observing schedules and subsequently, let the user specify an observing schedule to be changed.

Step 114: The CPU 65 determines whether or not an input to stop changing the observing schedule is accepted. If there is an input to stop changing (the case of YES), the CPU 65 returns to S102 and repeats the above-mentioned operation. If, on the other hand, there is an input specifying an observing schedule to be changed (the case of NO), the CPU 65 proceeds to S115.

Step 115: If an observing schedule to be changed is specified in S113, the CPU 65 displays the detail setting screen of imaging condition on the monitor 56a of the operation panel 56 (or a monitor of the computer 58). Then, the user changes the imaging condition in the observing schedule on the detail setting screen of imaging condition. Here, since the operation of the CPU 65 in S115 is common with that in S105, duplicate description is omitted.

Step 116: The CPU 65 calculates the observing duration of the incubation container 30 again, according to the change of imaging condition in S115. Here, since the operation of the CPU 65 in S116 is common with that in S106, duplicate description is omitted.

Step 117: The CPU 65 determines whether or not the observing duration acquired in S116 has increased from that before the change. If the observing duration has increased (the case of YES), the CPU 65 proceeds to S118. If, on the other hand, the observing duration is the same with, or has decreased from, before the change (the case of NO), the CPU 65 proceeds to S120.

Step 118: The CPU 65 determines whether or not overlap with other observing schedules set in the preceding or following time zone occurs due to increase of the observing duration of the observing schedule to be changed. If overlap of observing schedules occurs (the case of YES), the CPU 65 proceeds to S119. If, on the other hand, no overlap of observing schedules occurs (the case of NO), the CPU 65 proceeds to S120.

Step 119: The CPU 65 displays a warning that overlap of schedules occurs on the monitor 56a of the operation panel 56 (or a monitor of the computer 58). Subsequently, the CPU 65 returns to S114 without registering the observing schedule after change. In this case, the user must either cancel the change of the observing schedule or reset the imaging condition again.

Step 120: The CPU 65 registers the observing schedule after change by overwriting the schedule data of the second memory 64. In other words, since overlap of observing schedules does not occur in this case, the CPU 65 registers the observing schedule after change as it is. Subsequently, the CPU 65 returns to S102 and repeats the above-mentioned operation. Description of the flow chart of FIG. 11 is thus completed.

In the first embodiment, the CPU 65 calculates the observing duration of the incubation container 30 according to the imaging condition specified by the user. The CPU 65 then extracts a registrable time zone in which the observing sequence can be executed without overlapping with previously registered observing schedules, and displays the result on the monitor. Therefore, overlap of observing schedules of the incubation containers 30 can be preliminarily prevented by the user's selecting a time for executing the observing sequence from registrable time zones. Particularly, since the CPU 65 in the first embodiment preliminarily disables observing schedules other than those during a registrable time zone, overlap of observing schedules can be prevented more certainly.

Additionally, since the CPU 65 in the first embodiment provides a warning if overlap with other observing schedules occurs due to increase of observing duration when changing the previously registered observing schedule, overlap of observing schedules of the incubation containers 30 can be prevented more certainly.

Here, in the first embodiment, since the user can also register an observing schedule from a remote computer 58 coupled to the incubator 11 via a communication line 57, convenience of the device is enhanced.

(Description of Operation of Observing Sequence)

Figure 16:
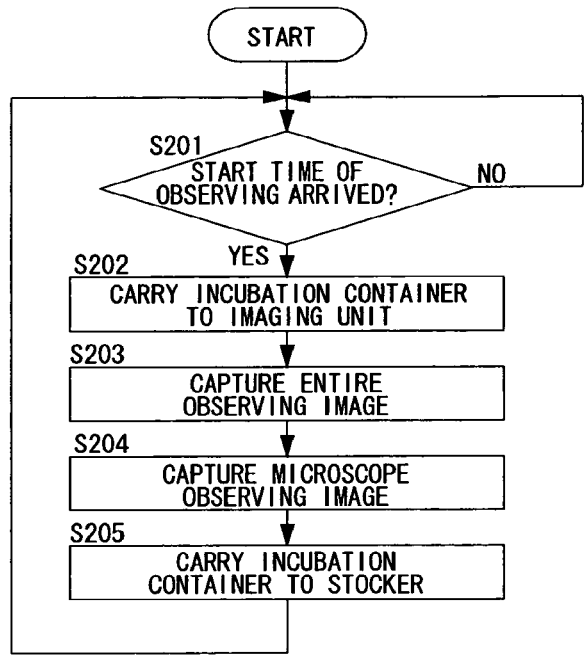
FIG. 16 is a flow chart explaining the operation of the CPU in the observing sequence.

Next, operation of the CPU 65 in the above-mentioned observing sequence will be described, referring to the flow chart of FIG. 16.

Step 201: The CPU 65 compares the observing schedule of the second memory 64 with the current time and date, and determines whether or not start time of observing the incubation container 30 has arrived. If the start time of observation has arrived (the case of YES), the CPU 65 proceeds to S202. If, on the other hand, it is not the start time of observing the incubation container 30 (the case of NO), the CPU 65 waits until the time of next observing schedule.

Step 202: The CPU 65 instructs the container carrying mechanism 27 to carry the incubation container 30 corresponding to the observing schedule. The container carrying mechanism 27 then carries out the specified incubation container 30 from the stocker 25, and places in on the sample stage 47 of the observing unit 28.

Step 203: The CPU 65 instructs the observing unit 28 to capture the entire observing image. The observing unit 28 turns on the second lighting section 52 to illuminate the incubation container 30, and captures the entire observing image of the incubation container 30 via the image pickup device of the container observing section 54.

Step 204: The CPU 65 instructs the observing unit 28 to capture the microscope observing image. The observing unit 28 turns on the first lighting section 51 to illuminate the incubation container 30, and captures the microscope observing image of the incubation container 30 via the image pickup device of the microscope observing section 53. In this occasion, the observing unit 28 captures the microscope observing image with an imaging condition (magnification of the objective lens, observing point inside the container, number of frames, etc) set by the user, based on the data of the observing schedule registered in the second memory 64.

Step 205: After the microscope observing image has been finished, The CPU 65 instructs the container carrying mechanism 27 to carry the incubation container 30. The container carrying mechanism 27 carries the specified incubation container 30 from the sample stage 47 of the observing unit 28 to a predefined housing position of the stocker 25, then terminates the observing sequence and proceeds to S201. Description of the flow chart of FIG. 16 is thus completed.

As thus described, with the incubator 11 of the first embodiment, automatic observing of samples in the incubation container 30 can be executed, based on the observing schedule.

(Description of Operation when Carrying Out the Incubation Container)

Figure 17:
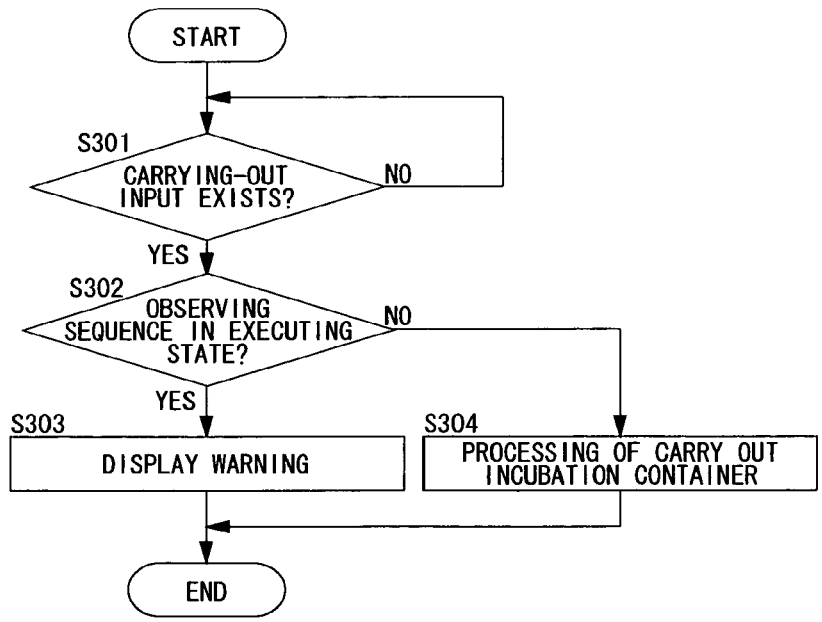
FIG. 17 is a flow chart explaining the operation of the CPU when carrying the incubation container out.

Next, operation of the CPU 65 when carrying out the incubation container 30 will be described, referring to the flow chart of FIG. 17.

Step 301: The CPU 65 determines whether or not an input that instructs to carry out the incubation container 30 is accepted from the input button 56b of the operation panel 56.

If an input that instructs to carry out the incubation container 30 is accepted (the case of YES), the CPU 65 proceeds to S302. If, on the other hand, there is no such input (the case of NO), the CPU 65 waits for an input that instructs to carry out the incubation container 30.

Step 302: The CPU 65 determines whether or not the incubation container 30 specified to be carried out by the carrying-out instruction input in S301 is in an executing state of the observing sequence. In the determination of S302, the CPU 65 may refer to the schedule data and regard the case as the above-mentioned executing state, in which the observing sequence is started within a certain period.

If the container to be carried out is in the execution state of the observing sequence (the case of YES), the CPU 65 proceeds to S303. If, on the other hand, the container to be carried out is not in the executing state (the case of NO), the CPU 65 proceeds to S304.

Step 303: The CPU 65 displays a warning that the container to be carried out is in an executing state of the observing sequence on the monitor 56a of the operation panel 56. Additionally, if a warning is displayed, the CPU 65 requires the user to provide an input confirming whether or not to carry out the incubation container 30 which is in an executing state of the observing sequence. The CPU 65 then carries the incubation container 30 out of the temperature-controlled room 15 by a process substantially similar to that of S304 which will be described below, only when the user chose to carry out the incubation container 30 in the above-mentioned confirmation input.

Such a warning display and confirmation input significantly reduce the risk that the user carries out the incubation container 30 by mistake during execution of the observing sequence.

Step 304: The CPU 65 instructs the container carrying in-and-out mechanism 26 and the container carrying mechanism 27 to discharge the incubation container 30 to be carried out from the temperature-controlled room 15. The container carrying mechanism 27 passes the specified incubation container 30 from the stocker 25 to the container carrying in-and-out mechanism 26. Then the CPU 65 opens the automatic door 19 of the carrying in-and-out opening 17, and causes the container carrying in-and-out mechanism 26 to discharge the incubation container 30 out of the temperature-controlled room 15. Description of the flow chart of FIG. 17 is thus completed.

(Description of an Exemplary Variation of the Registration Processing of the Observing Schedule)

Figure 18:
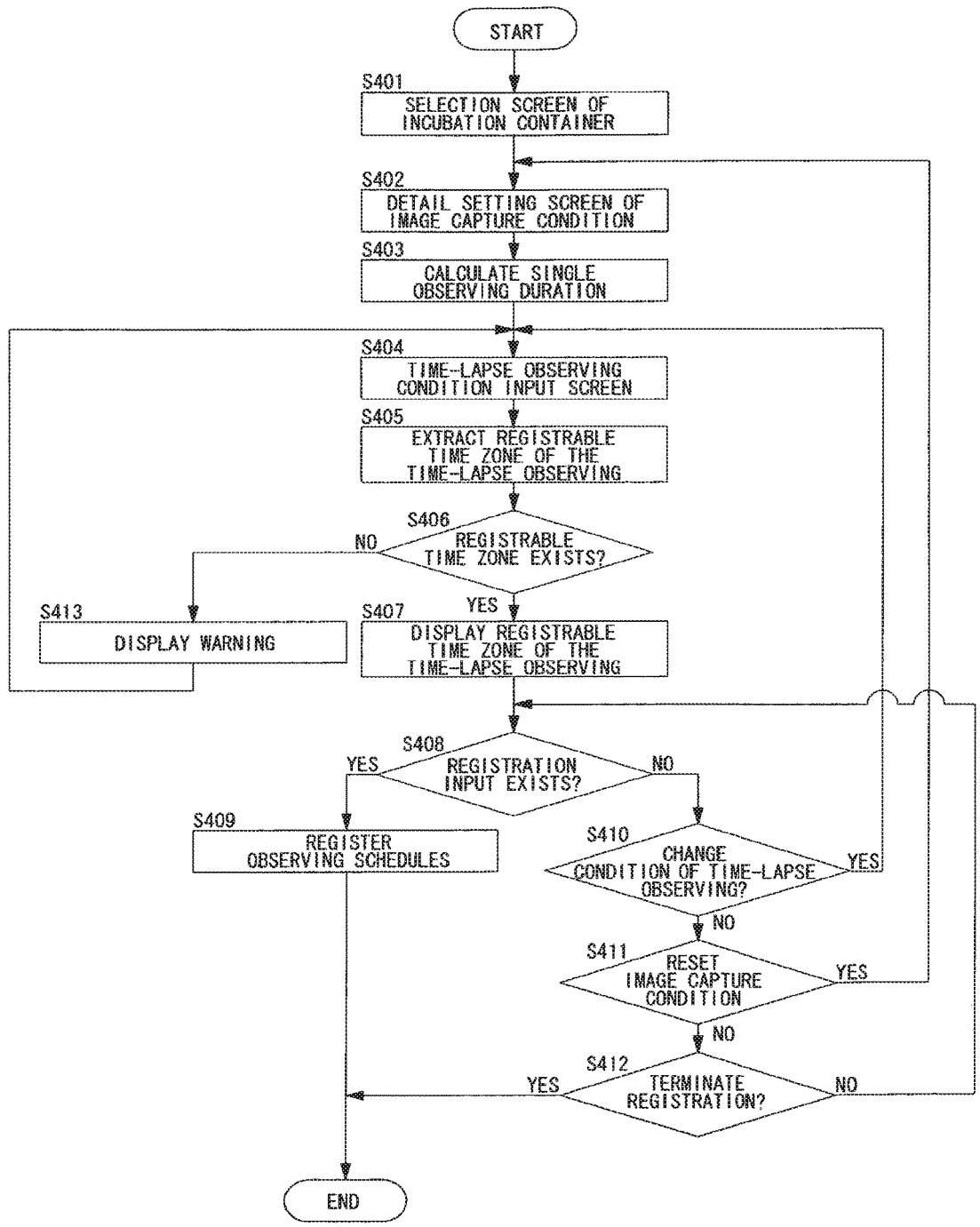
FIG. 18 is a flow chart illustrating the registration processing of the observing schedule according to a variation of the first embodiment.

Additionally, FIG. 18 shows an exemplary variation of the registration processing of the observing schedule. Here, since the arrangement of the incubator in the exemplary operation of FIG. 18 is common with the above-mentioned embodiment, duplicate description is omitted.

In the example of FIG. 18, the CPU 65 can execute collective registration of the observing schedule of the time-lapse observing. Here, for simplicity in the example of FIG. 18, description is given assuming the case of "newly registering an observing schedule".

Step 401: The CPU 65 displays a selection screen letting the user select an incubation container 30 for which an observing schedule is to be set on the monitor 56a of the operation panel 56 (or a monitor of the computer 58). Here, since the processing in S401 is common with that in S104 of FIG. 11, duplicate description will be omitted.

Step 402: The CPU 65 displays the detail setting screen of imaging condition on the monitor 56a of the operation panel 56 (or a monitor of the computer 58). Here, since the processing in S402 is common with that in S105 of FIG. 11, duplicate description is omitted.

Step 403: The CPU 65 calculates the observing duration of a single time-lapse observing, based on the inputs in S401 and S402. Here, since the processing in S403 is common with that in S106 of FIG. 11, duplicate description is omitted.

Step 404: The CPU 65 displays a screen for accepting an input of the condition of the time-lapse observing on the monitor 56a of the operation panel 56 (or a monitor of the computer 58).

Figure 19:
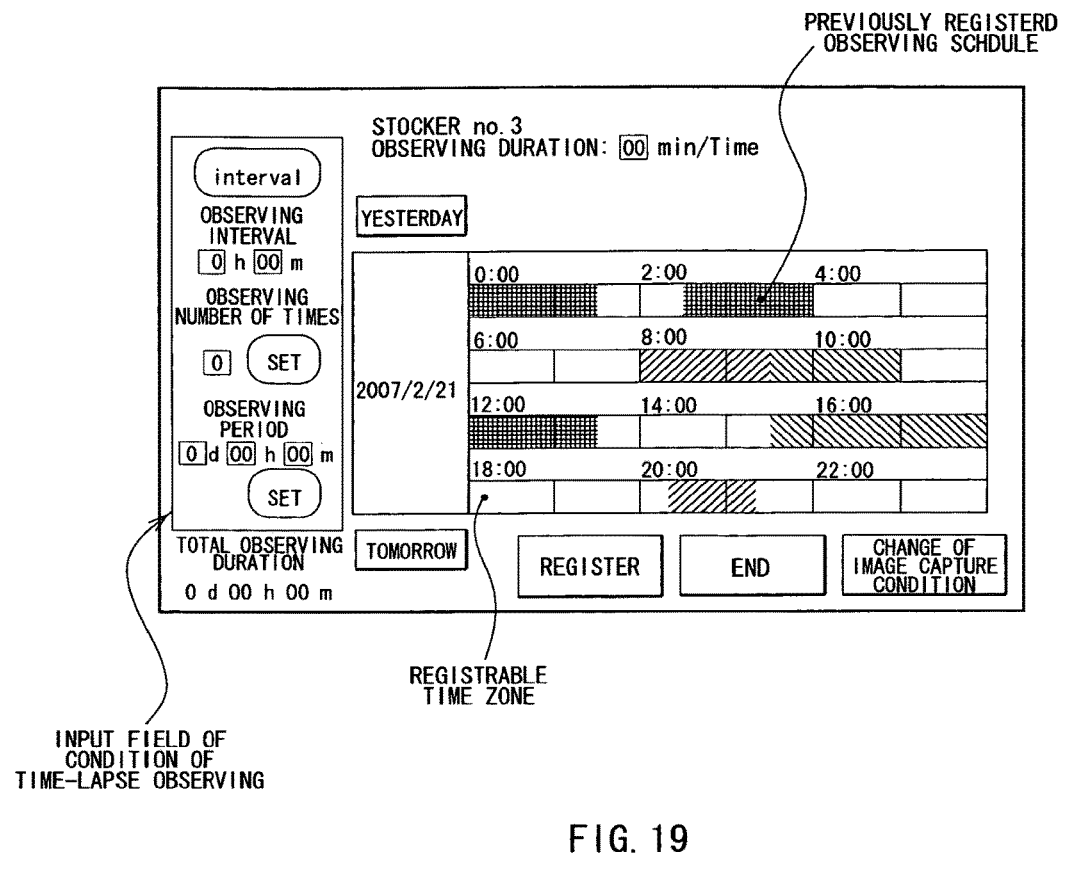

Here, an exemplary display screen in S404 is shown in FIG. 19. In the display screen (left-hand side of the screen of FIG. 19), interval, number of times, and period of the time-lapse observing can be input as the condition of the time-lapse observing. Then, the CPU 65 proceeds to S405, if (1) the SET button on the screen is pressed with the interval and number of times of the time-lapse observing having been input, or (2) the SET button on the screen is pressed with the interval and period of the time-lapse observing having been input. Here, the user's input on the display screen is performed from the input button 56b of the operation panel 56 (or an input device of the computer 58).

Step 405: The CPU 65 extracts a registrable time zone of the time-lapse observing, based on the condition of the time-lapse observing (S404). Specifically, the CPU 65 executes the following processing (1) to (4) in S405.

(1) The CPU 65 extracts, from the schedule data of the second memory 64, an idle-time having no observing schedule registered and being equal to or longer than the observing duration (acquired in S403).

(2) The CPU 65 tentatively sets a plurality of observing schedules of the incubation container 30, according to the time interval and number of times (or period) under the condition (S404) of the time-lapse observing, setting an arbitrary time-point in the above-mentioned idle-time (1) as the start time. Here, the period of a single observing schedule in the tentative setting corresponds to the observing duration acquired in S403.

(3) The CPU 65 determines whether or not each of the observing schedules tentatively set in (2) overlaps with previously registered observing schedules. If a tentatively set observing schedule overlaps with previously registered observing schedules, the CPU 65 determines that time-lapse observing is impossible with the tentatively set observing schedule. If, on the other hand, any of the tentatively set observing schedules does not overlap with previously registered observing schedules, the CPU 65 determines that time-lapse observing is possible with the tentatively set observing schedule and extracts the tentatively set observing schedule as a registrable time zone of the time-lapse observing.

(4) The CPU 65 changes the start time of the time-lapse observing and repeats the operations of (2) and (3). The CPU 65 thus determines whether or not time-lapse observing of the specified incubation container 30 is possible in the idle-time of (1).

Step 406: The CPU 65 determines whether or not it succeeded in extracting a registrable time zone of the time-lapse observing in S405. If the above-mentioned condition is satisfied (the case of YES), the CPU proceeds to S407. If, on the other hand, the above-mentioned condition is not satisfied (the case of NO), the CPU proceeds to S413.

Step 407: The CPU 65 displays the registrable time zone of the time-lapse observing (S405) on the monitor 56a of the operation panel 56 (or a monitor of the computer 58).

Here an exemplary display of the registrable time zone of S407 is shown in FIG. 19. In FIG. 19, the above-mentioned registrable time zone is listed on the right-hand side of the screen. In this occasion, the CPU 65 displays the registrable time zone, based on the first-time time-lapse observing. In other words, a time zone in which the previously registered observing schedule does not exist is displayed as an unregistrable time zone on the display screen of FIG. 19, if observing schedules overlap by executing time-lapse observing starting from that time zone. The CPU 65 then preliminarily disables, on the display screen of FIG. 19, registration of observing schedules other than during registrable time zones. In FIG. 19, registrable time zones of the time-lapse observing are shown as blank fields, whereas time zones in which time-lapse observing cannot be registered are shown by hatching.

Then, the user can specify a desired time zone among registrable time zones and register the observing schedule of the time-lapse observing in the second memory 64. In this occasion, the time zone specified by the user corresponds to the observing schedule of the first-time time-lapse observing. Here, the user's input of the registrable time zone on the display screen is performed via the input button 56b of the operation panel 56 (or an input device of the computer 58).

Step 408: The CPU 65 determines whether or not an input to register the observing schedule (for example, input via the registration button in FIG. 19) is accepted with the display screen of S407 being displayed. If the observing schedule is registered (the case of YES), the CPU 65 proceeds to S409. If, on the other hand, no observing schedule is registered (the case of NO), the CPU 65 proceeds to S410.

Step 409: The CPU 65 collectively registers a plurality of observing schedules of the time-lapse observing in the schedule data of the second with memory 64. Subsequently, the CPU 65 terminates the registration processing of observing schedules of the time-lapse observing.

Step 410: The CPU 65 determines whether or not a manipulation of changing the condition of the time-lapse observing is accepted with the display screen of S407 being displayed. If a manipulation of changing the condition of the time-lapse observing is executed (the case of YES), the CPU 65 returns to S404 and repeats the above-mentioned operation. If, on the other hand, no manipulation of changing the condition of the time-lapse observing is executed (the case of NO), the CPU 65 proceeds to S411.

Step 411: The CPU 65 determines whether or not an input to reset the imaging condition (for example, input via the change imaging condition button in FIG. 19) is accepted with the display screen of S407 being displayed. If there is an input to reset the imaging condition (the case of YES), the CPU 65 returns to S402 and repeats the above-mentioned operation. If, on the other hand, there is no input resetting the imaging condition (the case of NO), the CPU 65 proceeds to S412.

Step 412: The CPU 65 determines whether or not an input to terminate the registration (for example, input via END button in FIG. 19) is accepted with the display screen of S407 being displayed. If there is an input to terminate the registration (the case of YES), the CPU 65 terminates the registration processing of observing schedules of the time-lapse observing. If, on the other hand, there is no input to terminate the registration (the case of NO), the CPU 65 returns to S408 and repeats the above-mentioned operation.

Step 413: The CPU 65 displays a warning (the screen displaying the warning is not shown here) that a registrable time zone cannot be extracted on the monitor 56a of the operation panel 56 (or a monitor of the computer 58). The CPU 65 then returns to S404 and accepts input of the time-lapse observing condition again.

Here, when displaying the warning in S413, the CPU 65 may display a list of the recommended condition of the time-lapse observing for which a registrable time zone can be extracted (interval, number of times, or period of the time-lapse observing). The user can thus easily recognize the condition under which a schedule of the time-lapse observing can be registered, whereby convenience of the incubator improves.

As an example, the CPU 65 sets the number of times (or period) of the time-lapse observing to be smaller than the input value, and acquires a registrable time zone of the time-lapse observing by a similar calculation as that in S405. Additionally, as another example, the CPU 65 sets the interval of the time-lapse observing as a value different from the input value, and acquires registrable time zone of the time-lapse observing by a similar calculation as that in S405. Then, if a registrable time zone of the time-lapse observing is extracted by the above-mentioned processing, the CPU 65 displays the parameter of the above-mentioned recommended condition of time-lapse observing and the time zone which is registrable under the recommended condition on the monitor 56a or the like. Description of the flow chart of FIG. 18 is thus completed.

With the exemplary variation shown in FIG. 18, the CPU 65 presents a registrable time zone in which time-lapse observing sequence can be executed without overlapping with previously registered observing schedules. Thus, overlap of observing schedules can be preliminarily prevented by the users selecting a schedule of the time-lapse observing from registrable time zones.

Description of Second Embodiment

Operation of the CPU 65 in the processing of registering the observing schedule in the second embodiment will be described below, referring to the flow chart of FIG. 20. Here, manipulation of registering the observing schedule of the incubation container 30 is executed by the user via the operation panel 56 of the incubator 11 or the computer 58 coupled to the incubator 11. Since the arrangement of the incubator, the operation of the observing sequence, and the operation when carrying out the incubation container in the second embodiment are common with that of the first embodiment, duplicate description is omitted.

Figure 20:
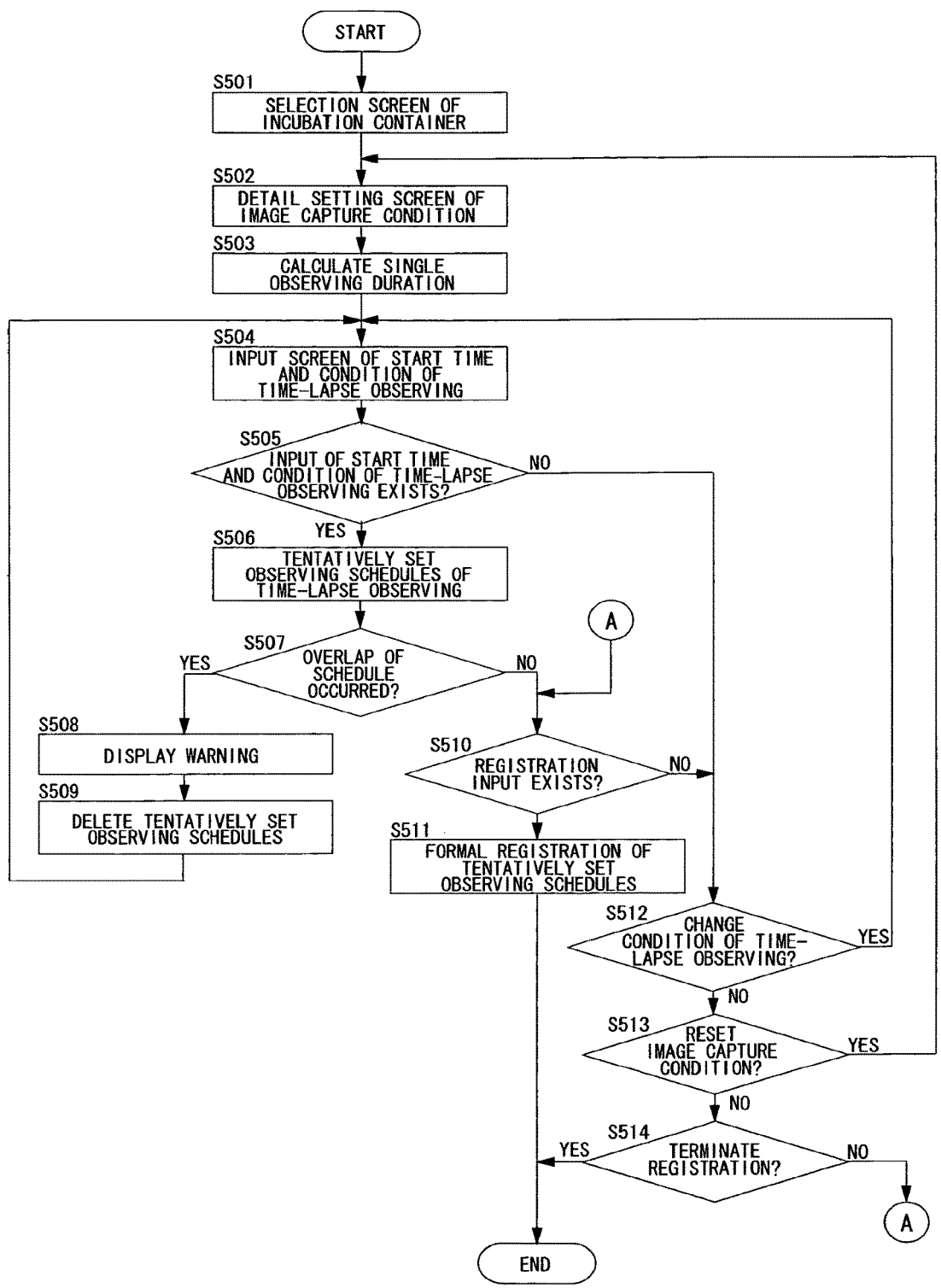
FIG. 20 is a flow chart illustrating the registration processing of the observing schedule relating to a second embodiment.

In the example of FIG. 20, the CPU 65 can execute collective registration of the observing schedule of the time-lapse observing. Here, in the example of FIG. 20, description is given assuming the case of "newly register observing schedule", for simplicity.

Step 501: The CPU 65 displays a selection screen letting the user select an incubation container 30 for which an observing schedule is set on the monitor 56a of the operation panel 56 (or a monitor of the computer 58). Here, since the processing in S501 is common with S104 of FIG. 11 described in the first embodiment, duplicate description is omitted.

Step 502: The CPU 65 displays the detail setting screen of imaging condition on the monitor 56a of the operation panel 56 (or a monitor of the computer 58). Here, since the processing in S502 is common with S105 of FIG. 11 described in the first embodiment, duplicate description is omitted.

Step 503: The CPU 65 calculates the duration of a single incubation observation of the container 30. Here, since the processing in S503 is common with S106 of FIG. 11 described in the first embodiment, duplicate description is omitted.

Step 504: The CPU 65 displays a screen for accepting the input of start time and condition of the time-lapse observing on the monitor 56a of the operation panel 56 (or a monitor of the computer 58).

Here, an exemplary display screen in S504 is shown in FIG. 19. A list of previously registered observing schedules is displayed on the right-hand side of the screen in FIG. 19.

In FIG. 19, previously registered observing schedules are shown by hatching, whereas time zones which can be specified as start time of the time-lapse observing are shown as blank fields. Then, the user can specify a desired time zone among the above-mentioned specifiable time zones, and input the start time of the time-lapse observing for the CPU 65.

In the display area shown on the left-hand side of the screen of FIG. 19, interval, number of times, and period of the time-lapse observing can be input as the condition of the time-lapse observing.

The CPU 65 then fixes the condition of the time-lapse observing if (1) the confirmation button (SET) on the screen is pressed with the interval and number of times of the time-lapse observing having been input, or (2) the confirmation button (SET) on the screen is pressed with the interval and period of the time-lapse observing having been input.

Step 505: The CPU 65 determines whether or not both the start time of the time-lapse observing and the condition of the time-lapse observing have been input, with the display screen of S504 being displayed. For example, the CPU 65 determines that the start time of the time-lapse observing and the condition of the time-lapse observing have been input if the confirmation button (SET) on the left-hand side of the screen is pressed with the start time of the time-lapse observing having been specified on the display screen of FIG. 19. If the above-mentioned condition is satisfied (the case of YES), the CPU 65 proceeds to S506. If, on the other hand, the above-mentioned condition is not satisfied (the case of NO), the CPU 65 proceeds to S512.

Step 506: Based on the start time specified in S505, the CPU 65 tentatively sets a plurality of observing schedules of the incubation container 30, in accordance with the time interval and number of times (or period) according to the condition (S505) of the time-lapse observing. Here, the period of a single observing schedule in the tentative setting corresponds to the observing duration calculated in S503.

Step 507: The CPU 65 determines whether or not any of the observing schedules tentatively set in S506 overlaps with previously registered observing schedules. If the above-mentioned requirement is satisfied (the case of YES), the CPU 65 proceeds to S508. If, on the other hand, the requirement is not satisfied (the case of NO), the CPU 65 proceeds to S510.

Step 508: The CPU 65 displays a warning (the screen displaying the warning is not shown here) that overlap with previously registered observing schedules is occurring on the monitor 56a of the operation panel 56 (or a monitor of the computer 58).

In this occasion the CPU 65 displays, on the monitor 56a or the like, detailed information of the previously registered schedule (identification information of the incubation container 30 and time of day of the observing schedule) overlapping with the above-mentioned tentatively set observing schedule. Therefore the user can recognize in a concrete manner with which schedule the overlapping is occurring.

Step 509: The CPU 65 deletes the observing schedule of the time-lapse observing which has been tentatively set in S506, returns to S504, and repeats the above-mentioned operation. In this manner, the user can change the condition or start time of the time-lapse observing to avoid overlap of schedules.

Step 510: The CPU 65 determines whether or not an input to register the observing schedule (for example, input via the registration button in FIG. 19) is accepted with the display screen of S504 being displayed. If the above-mentioned requirement is satisfied (the case of YES), the CPU 65 proceeds to S511. If, on the other hand, the requirement is not satisfied (the case of NO), the CPU 65 proceeds to S512.

Step 511: The CPU 65 formally registers, collectively into the schedule data of the second memory 64, the observing schedule of the time-lapse observing tentatively set in S506. Subsequently, the CPU 65 terminates the processing of registering the observing schedule of the time-lapse observing.

Step 512: The CPU 65 determines whether or not a manipulation of changing the condition of the time-lapse observing is accepted with the display screen of S504 being displayed. If a manipulation of changing the condition of the time-lapse observing is accepted (the case of YES), the CPU 65 returns to S504 and repeats the above-mentioned operation. If, on the other hand, no manipulation of changing the condition of the time-lapse observing is accepted (the case of NO), the CPU 65 proceeds to S513.

Step 513: The CPU 65 determines whether or not an input to reset the imaging condition (for example, input via the change imaging condition button in FIG. 19) is accepted with the display screen of S504 being displayed. If there is an input to reset the imaging condition (the case of YES), the CPU 65 returns to S502 and repeats the above-mentioned operation. If, on the other hand, there is no input to reset the imaging condition (the case of NO), the CPU 65 proceeds to S514.

Step 514: The CPU 65 determines whether or not input ending the registration (for example, input via END button in FIG. 19) is accepted with the display screen of S504 being displayed. If there is an input ending the registration (the case of YES), the CPU 65 terminates the registration processing of the observing schedule of the time-lapse observing. If, on the other hand, there is no input ending the registration (the case of NO), the CPU 65 returns to S510 and repeats the above-mentioned operation. Description of the flow chart of FIG. 20 is thus completed.

In the second embodiment, the CPU 65 determines whether or not the tentatively set schedule of the time-lapse observing overlaps with previously registered observing schedules. Then, if an overlap between the both schedules occurs, the CPU 65 warns the user. Therefore, in the second embodiment, overlap of observing schedules can be preliminarily prevented when collectively registering the observing schedules of the time-lapse observing.

Supplementary Notes on Embodiments (1) Arrangement of respective components of the incubator 11 of the present invention is not limited to the above-mentioned embodiment. For example, the present invention can also be applied to a multi-gas incubator which can regulate, in addition to carbon dioxide concentration, at least either oxygen concentration or nitrogen concentration. Additionally, with the present invention, humidity may be regulated using a humidifying plate which reserves humidifying water and a temperature regulating device which controls water temperature of the humidifying plate. Furthermore, the temperature regulating device 21 in the above-mentioned embodiments may be replaced by a known arrangement such as a combination of a heater unit and a refrigerant recycling system, for example (all of which not shown).

(2) In the above-mentioned embodiments, value of time of the first and second data, or unit time of the schedule data can be changed as appropriate. Additionally, in the above-mentioned embodiments, although the carrying period of the first data is treated as a single value, a plurality of values may be registered in the first memory 63 as the carrying period of the first data, for example, the carrying period may be changed according to the position on the stocker 25.

(3) In the above-mentioned embodiments, the warning means of the incubator 11 to the user may be replaced by voice output such as a buzzer (not shown), for example.

(4) In an exemplary variation of the first embodiment shown in FIG. 18, if a registrable time zone of the time-lapse observing cannot be extracted (the case of NO of S406), the CPU 65 may eliminate the overlap with previously registered observing schedules by shifting the time zone in which overlap is occurring among the observing schedules of the time-lapse observing.

(5) In the above-mentioned second embodiment, if a tentatively set observing schedule overlaps with previously registered observing schedules (the case of YES of S507), the CPU 65 may eliminate the overlap with previously registered observing schedules by shifting the time zone of the tentatively set observing schedule.

(6) When displaying the warning in S508 of the above-mentioned second embodiment, the CPU 65 may list the recommended condition of the time-lapse observing (start time of the time-lapse observing, interval of the time-lapse observing, number of times or period of the time-lapse observing).

For example, the CPU 65 fixes either the condition of the time-lapse observing (interval, number of times) or the start time of the time-lapse observing, and generates the tentatively set observing schedule by changing other parameters. The CPU 65 determines the tentatively set observing schedule to be a recommended condition if it does not overlap with previously registered observing schedules, and displays respective parameters on the monitor 56a or the like. Here, it may be arranged such that the CPU 65 automatically executes calculation of the recommended condition when some of the parameters (for example, with either the start time or the condition of the time-lapse observing (interval, number of times, etc.) specified) are input in the display screen of S504.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

The invention claimed is:

1. An incubator comprising:
   a temperature-controlled room configured to maintain an interior of the temperature-controlled room to a predefined environment condition;
   an imaging section configured to capture images of a condition of samples within an incubation container in the temperature-controlled room;
   a carrying mechanism configured to move the incubation container; and a processor programmed to:
    accept, from a user, a first input selection of a selectable incubation container, and a second input selection of an imaging condition;
    calculate an observation duration of the selected incubation container based on stored first data and stored second data according to the selected imaging condition, the stored first data indicating a carrying period of the incubation container by the carrying mechanism, and the stored second data indicating an imaging duration of the imaging section; and
    extract, based on stored schedule data and the calculated observation duration, a registrable time zone, the registrable time zone being a time zone in which the observation sequence of the specified incubation container can be executed without overlapping with a plurality of observation schedules that have been previously-stored.

2. The incubator according to claim 1, wherein the processor is further programmed to:
    register, based on a user's input, one of the observation schedules of the specified incubation container into the stored schedule data, and
    disable registration of the one of the observation schedules other than during the registrable time zone.

3. The incubator according to claim 2, wherein the processor is further programmed to:
    recalculate the observation duration of the selected incubation container if there is an input changing the imaging condition after registration of the one of the observation schedules, and
    output a notification to warn the user if overlap of the observation schedules occurs due to increase of the observation duration.

4. The incubator according to claim 1, wherein
    the carrying mechanism carries the selected incubation container out from the temperature-controlled room, and
    the processor is further programmed to: while the observation sequence of the selected incubation container to be carried out is being executed, outputting a notification to warn the user before the carrying out is executed.

5. The incubator according to claim 1, wherein the processor is further programmed to: output, a display, a registration status of one of the observation schedules with regard to any of the incubation containers, based on the stored schedule data.

6. The incubator according to claim 1, wherein the processor is further programmed to:
    receive the first input selection and the second input selection from an external computer, and
    transmit, to a display of the external computer, the registrable time zone.

7. The incubator according to claim 1, wherein the processor is further programmed to:
    accept a third input defining a condition of a time-lapse observation of the specified incubation container,
    set the plurality of observation schedules of the specified incubation containers respectively having different observation times, according to the condition of the time-lapse observation, and
    extract, as the registrable time zone, a time zone in which each of the observation schedules of the time-lapse observation can be executed without overlapping with the observation schedules being previously stored.

8. The incubator according to claim 7, wherein the processor is further programmed to: output, the display, as the registrable time zone in the time-lapse observation, a first-time time zone of the time-lapse observation.

9. The incubator according to claim 7, wherein the processor is further programmed to: output, the display, at least one of a warning and a presentation of the condition of the time-lapse observation for which the registrable time zone can be extracted, when the registrable time zone cannot be extracted.

10. The incubator according to claim 7, wherein the processor is further programmed to: shift one of the observation schedules of the time-lapse observation, when the registrable time zone cannot be extracted.

11. A schedule management method for an incubator, the method comprising:
    accepting a first input selection of an incubation container, and a second input selection of an imaging condition;
    calculating an observation duration of the selected incubation container based on first data and second data according to the selected imaging condition, the first data indicating a carrying period of the incubation container by a carrying mechanism, and the second data indicating an imaging duration of an imaging section; and
    extracting, based on stored schedule data and the calculated observation duration, a registrable time zone, the registrable time zone being a time zone in which an observation sequence of the selected incubation container can be executed without overlapping with a plurality of observation schedules that have been previously-stored, each of the previously-stored observation schedules including a start time and an observation sequence duration stored in association with one of the incubation containers.

12. The schedule management method according to claim 11, further comprising:
    receiving the first input and the second input from a computer coupled to the incubator, and
    transmitting to a display of the coupled computer the registrable time zone.

13. A non-transitory computer readable storage medium storing computer program instructions that, when executed by a computer, cause the computer to:
    accept a first input selection of an incubation container, and a second input selection of an imaging condition;
    calculate an observation duration of the selected incubation container based on first data and second data according to the selected imaging condition, the first data indicating a carrying period of the incubation container by a carrying mechanism, and the second data indicating an imaging duration of an imaging section; and
    extract, based on stored schedule data, and the calculated observation duration, a registrable time zone, the registrable time zone being a time zone in which an observation sequence of the selected incubation container can be executed without overlapping with a plurality of observation schedules that have been previously-stored, each of the previously-stored observation schedules including a start time and an observation sequence duration stored in association with one of the incubation containers.

14. The non-transitory computer readable storage medium storing the program according to claim 13, wherein
    the computer is coupled to the incubator, and a display, and the program further comprises instructions that cause the computer to: transmit, to the display, the registrable time zone.

15. An incubator comprising:
a camera configured to capture images in a temperature-controlled room; and
a processor programmed to:
   accept, from a user, a first input selection of an incubation container in the temperature-controlled room, and a second input selection of an imaging condition;
   calculate an observation duration of the selected incubation container based on stored first data and stored second data according to the selected imaging condition, the stored first data indicating a carrying period of the incubation container by a carrying mechanism, and the stored second data indicating an imaging duration of the camera; and
   extract, based on stored schedule data and the calculated observation duration, a registrable time zone, the registrable time zone being a time zone in which an observation sequence of the specified incubation container can be executed without overlapping with a plurality of observation schedules that have been previously-stored.

16. An incubator comprising:
a camera configured to capture images in a temperature-controlled room; and
a processor programmed to:
   accept, from a user, a first input selection of an incubation container in the temperature-controlled room, and a second input selection of an imaging condition;
   calculate an observation duration of the selected incubation container based on stored first data and stored second data according to the selected imaging condition, the stored first data indicating a carrying period of the incubation container by a carrying mechanism, and the stored second data indicating an imaging duration of the camera; and
   extract, based on stored schedule data and the calculated observation duration, a registrable time zone, the registrable time zone being a time zone in which an observation sequence of the specified incubation container can be executed without overlapping with a plurality of observation schedules that have been previously-stored, wherein the processor is further programmed to: control the camera and the carrying mechanism to automatically execute an observation sequence of the incubation container.

17. The incubator according to claim 16, wherein each of the observation schedules includes a start time and an observation duration of the observation sequence.

18. The incubator according to claim 16, further comprising:
   a first memory that stores the stored first data indicating the carrying period of the incubation container by the carrying mechanism, and the stored second data indicating the imaging duration of the imaging section; and
   a second memory that stores the stored schedule data including the plurality of observation schedules.

\* \* \* \* \*